US009875336B2

(12) United States Patent
Han et al.

(10) Patent No.: US 9,875,336 B2
(45) Date of Patent: Jan. 23, 2018

(54) SPATIAL ARITHMETIC METHOD OF SEQUENCE ALIGNMENT

(71) Applicants: Sherwin Han, Portsmouth, RI (US); Aihua Pan, Beijing (CN)

(72) Inventors: Sherwin Han, Portsmouth, RI (US); Aihua Pan, Beijing (CN)

(*) Notice: Subject to any disclaimer, the term of this patent is extended or adjusted under 35 U.S.C. 154(b) by 10 days.

(21) Appl. No.: 14/854,302

(22) Filed: Sep. 15, 2015

(65) Prior Publication Data

US 2016/0004816 A1 Jan. 7, 2016

Related U.S. Application Data

(63) Continuation of application No. PCT/US2014/027455, filed on Mar. 14, 2014.

(60) Provisional application No. 61/798,848, filed on Mar. 15, 2013.

(51) Int. Cl.
*G01N 33/50* (2006.01)
*G06F 19/22* (2011.01)

(52) U.S. Cl.
CPC ................................ *G06F 19/22* (2013.01)

(58) Field of Classification Search
None
See application file for complete search history.

(56) References Cited

U.S. PATENT DOCUMENTS

| | | | |
|---|---|---|---|
| 6,038,392 A | 3/2000 | Ashar | |
| 6,247,164 B1 | 6/2001 | Ashar | |
| 6,611,841 B1 | 8/2003 | Han | |
| 6,728,728 B2 | 4/2004 | Spiegler | |
| 7,120,569 B2 | 10/2006 | Arroyo-Figueroa | |
| 7,194,710 B2 | 3/2007 | Prasad | |
| 7,418,369 B2 | 8/2008 | Moskewicz | |
| 7,543,266 B2 | 6/2009 | Brown | |
| 7,565,634 B1 | 7/2009 | Boyd | |
| 9,031,890 B2 | 5/2015 | Han | |
| 2003/0224384 A1 | 12/2003 | Sayood | |
| 2005/0069954 A1 | 3/2005 | Sakai | |
| 2005/0182273 A1 | 8/2005 | Eh | |
| 2005/0182773 A1 | 8/2005 | Feinsmith | |
| 2009/0192963 A1 | 7/2009 | Sankaranarayanan | |
| 2009/0319461 A1 | 12/2009 | Meek | |
| 2010/0184609 A1* | 7/2010 | Passetti | G06F 19/26 506/8 |
| 2011/0010412 A1 | 1/2011 | Macready | |
| 2013/0041593 A1* | 2/2013 | Galinsky | G06F 19/22 702/20 |
| 2013/0179378 A1 | 7/2013 | Han | |
| 2014/0289181 A1 | 9/2014 | Han | |
| 2015/0074024 A1 | 3/2015 | Han | |
| 2016/0012339 A1 | 1/2016 | Han | |

FOREIGN PATENT DOCUMENTS

WO 2014152541 A1 9/2014
WO 2014165752 A1 10/2014

OTHER PUBLICATIONS

Cook, S., "The P versus NP Problem." Manuscript prepared for the Clay Mathematics Institute for the Millennium Prize Problems. (Apr. 2000) 12 pp. Available from the Clay Mathematics Institute.
Han, Sherwin, "Hierarchical Dual Memory Structure Determines Cognitive Logic of the Human Brain," in: Proceedings of 7th IEEE International Conference on Cognitive Informatics (ICCI 2008), pp. 332-340, Aug. 14-16, 2008.
Han et al., "3-SAT Polynomial Solution of Knowledge Recognition Algorithm," arXiv:1009.3687, Submitted to Cornell University Library on Sep. 20, 2010. 5 pp. Available at: http://arxiv.org/pdf/1009.3687v12.pdf.
Karp, R., "Reducibility Among Combinatorial Problems." in R. E. Miller and J. W. Thatcher (editors). Complexity of Computer Computations. New York: Plenum. pp. 85-103. (1972).
List of sequence alignment software, Wikipedia, the free encyclopedia, http://en.wikipedia.org, Available at: http://en.wikipedia.org/w/index.php?oldid=488518716, 20 pages, Retrieved on May 1, 2012, Creative Commons Attribution-Share Alike 3.0 Unported, Wikimedia Foundation, USA.
Parker, Brian J., et al., "New families of human regulatory RNA structures identified by comparative analysis of vertebrate genomes," Genome Research 2011, vol. 21, No. 11, pp. 1929-1943, Oct. 12, 2011. Available at: http://genome.cship.org/content/21/11/1929.full.pdf+html.
Sequence alignment—Wikipedia, the free encyclopedia, http://en.wikipedia.org, Available at: https://en.wikipedia.org/w/index.php?title.Sequence_alignment&printable=yes1%20of, 14 pages, Retrieved on May 1, 2012, Wikimedia Foundation, USA.
Wen, H., "Knowledge Recognition Algorithm enables P = NP," arXiv:1009.0884, Submitted to Cornell University Library, Sep. 2010, pp. 1-3.
Wen, H., "Mirrored Language Structure and Innate Logic of the Human Brain as a Computable Model of the Oracle Turing Machine," arXiv preprint arXiv:1006.2495, Jun. 2010, 2 pages, Cornell University Library, Ithaca, NY, USA.
Zhang, L., Madigan, C. F., Moskewcz, M. W. , Andmalik, S. 2001. "Efficient conflict driven learning in a Boolean satisfiability solver." In Proceedings of the International Conference on Computer-Aided Design (ICCAD 2001). 279-285.
Zhou, Jiayu, et al., "Unified Hierarchical Iterate Model of Human Conceptualization and Cognition," in: Proceedings of 8th IEEE International Conference on Cognitive Informatics (ICCI 2009), pp. 44-51, Jun. 14-17, 2009.
"A Probabilistic 3-SAT Algorithm Further Improved" ; Thomas Hofmeister, Uwe Schoning, Rainer Schuler, Osamu Watanabe. Dept. of Mathematical arid Computing Sciences, Tokyo Institute of Technology, Meguro-ku Ookayama, Tokyo 152-8552, Japan. H. Alt and A. Ferreira (Eds.): STACS 2002, LNCS 2285, pp. 192-202, 2002. Springer-Verlag Berlin Heidelberg 2002.

* cited by examiner

*Primary Examiner* — Jason Sims
(74) *Attorney, Agent, or Firm* — Blueshift IP, LLC; Robert Plotkin

(57) ABSTRACT

A computer system aligns two or more sequences with each other to identify similarities and differences between the aligned sequences. The sequences may, for example, represent proteins. The system performs alignment quickly and accurately by representing the sequences as perceptual information and conceptual information having mappings between them in a knowledgebase, and then performing the alignment based on the representations of the sequences in the knowledgebase. The alignment may be performed in polynomial time, regardless of the number of sequences that are aligned.

10 Claims, 11 Drawing Sheets

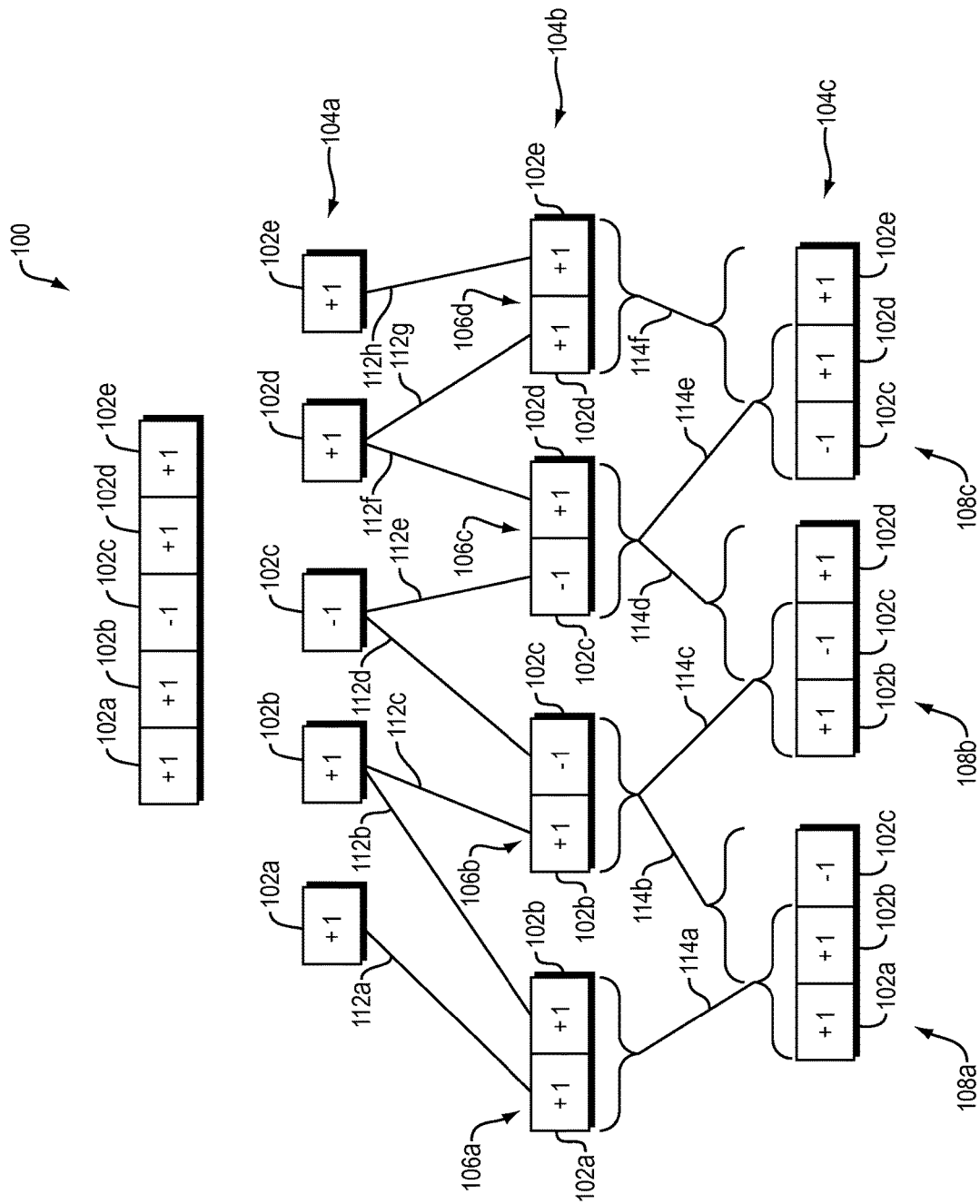

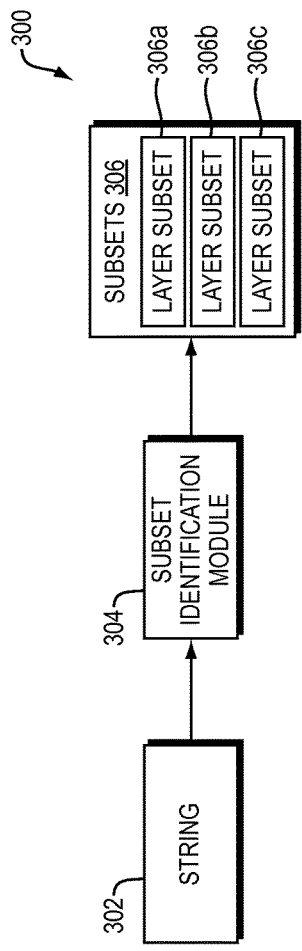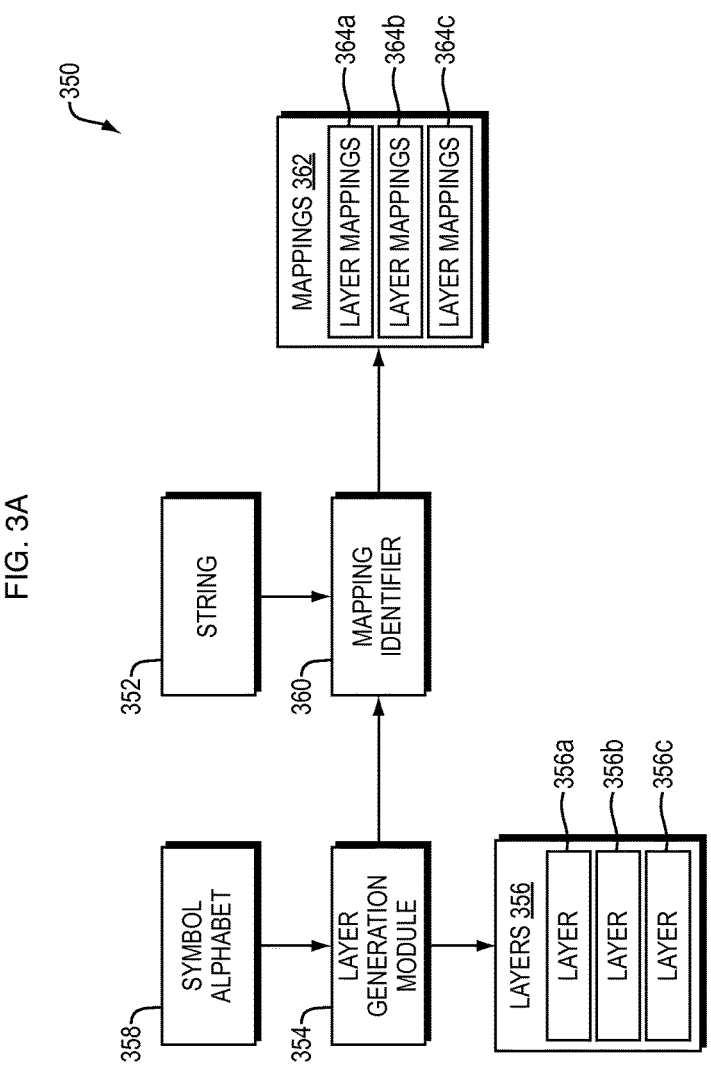

SPATIAL ARITHMETIC METHOD OF SEQUENCE ALIGNMENT

BACKGROUND

Sequence alignment involves arranging two or more sequences to identify similar regions within those sequences. For example, protein alignment involves arranging the sequences of two or more proteins to identify similar regions within those sequences. The outcome of a particular protein sequence alignment may indicate functional, structural, or evolutionary relationships between the aligned sequences. Although alignment may be applied to sequences representing any kind of information, some of the description below will refer to alignment of sequences representing proteins merely as one illustrative example.

The results of a particular protein alignment usually is represented by displaying each protein sequence horizontally as a sequence of letters representing the proteins in the sequence, with letter sequences arranged vertically, so that similar regions within each sequence are aligned vertically with each other. Although the description herein refers primarily to protein alignment, the same or similar techniques may be used to align other kinds of sequences, such as DNA and RNA sequences. All of these are examples of "sequence alignment."

Alignment typically involves identifying: (1) overlaps (identical or similar regions) between the aligned sequences, also referred to as intersections; (2) differences, such as a region that is contained within one of the aligned sequences but not another; (3) complements, which represent opposites within the aligned sequences, as in the case in which one aligned sequence contains a 1 and another aligned sequence contains a −1 at the same or similar position; and (4) unions, which represent all of the unique elements in some or all of two or more of the aligned sequences.

A wide variety of techniques for performing sequence alignment have been developed, such as dot-matrix methods, dynamic programming-based methods, progressive methods, methods based on hidden Markov models, and methods that use artificial neural networks. Regardless of the kind of sequence alignment technique that is used, aligning very large sequences causes the amount of computational resources (i.e., memory and/or processing) required to perform the alignment to increase exponentially. In general, the number of computations required to align sequences of length n is $n^2$. As a result, traditional sequence alignment techniques quickly become unwieldy for aligning sequences as the size of the sequences grows.

What is needed, therefore, are improved techniques for performing sequence alignment efficiently and effectively.

SUMMARY

A computer system aligns two or more sequences with each other to identify similarities and differences between the aligned sequences. The sequences may, for example, represent proteins. The system performs alignment quickly and accurately by representing the sequences as perceptual information and conceptual information having mappings between them in a knowledgebase, and then performing the alignment based on the representations of the sequences in the knowledgebase. The alignment may be performed in polynomial time, regardless of the number of sequences that are aligned.

Other features and advantages of various aspects and embodiments of the present invention will become apparent from the following description and from the claims.

BRIEF DESCRIPTION OF THE DRAWINGS

FIG. 1 is a diagram illustrating an example of a string representing a sequence decomposed into a plurality of layers according to one embodiment of the present invention;

FIGS. 3A-3B are diagrams illustrating systems for generating mappings between strings and layers according to one embodiment of the present invention;

DETAILED DESCRIPTION

Embodiments of the present invention are directed to improved techniques for aligning sequences, such as protein sequences, DNA sequences, and RNA sequences. In general, embodiments of the present invention use iterative sets to perform sequence alignment, and therefore represent a significant departure from previous sequence alignment techniques. Technology that is capable of processing iterative set operations is described in more detail in the above-referenced U.S. Pat. No. 6,611,841.

Embodiments of the present invention are based on an understanding of, and operate in a manner that is analogous to, the operation of the human brain. For example, consider the system of FIG. 5, which is modeled on the operation of the human brain, and which is described in more detail in the above-referenced U.S. Pat. No. 6,611,841. The system contains an object 500, which may, for example, be an object in the physical world, such as a bird, a table, or a person. The object 500 may, however, be an abstract object, such as a number. The system includes a first memory 501, which stores data representing perceptions, such as one or more perceptions of the object 500 and of other objects (not shown). The memory 501, therefore, is also referred to herein as a "perceptual memory."

Figure 5:
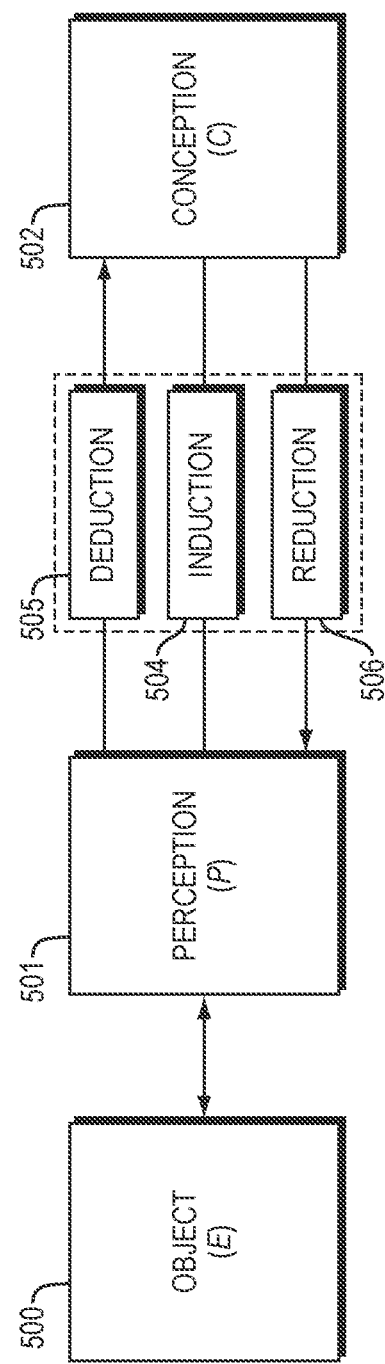
FIG. 5 is a dataflow diagram of a system for representing relationships between perceptual information and conceptual information according to one embodiment of the present invention.

The system of FIG. 5 also includes a second memory 502, which stores data representing conceptions (also referred to herein as concepts and classes). The system also includes an induction module 504, which recognizes (learns) relationships between the perceptions (representations of objects) stored in the perceptual memory 501 and the concepts stored in the conceptual memory 502, using a process of induction. For each relationship that the induction module 504 learns between a perception in the perceptual memory 501 and a concept in the conceptual memory 502, the induction module 504 generates and stores a two-way mapping between the perception and the concept. The process performed by the induction module 504 of generating and storing such mappings for an increasingly large number of perceptions and corresponding concepts models the learning process performed by the human brain. The resulting set of mappings is an example of a "knowledgebase" as that term is used herein.

For any given perception in the perceptual memory 501 and corresponding concept in the conceptual memory 502, the concept may be at the same level of abstraction as the perception, or at a higher level of abstraction than the perception. For example, the perception representing the object "bird" may correspond to the concept of "bird," in which case the concept is at the same level of abstraction as the perception. As another example, the perception representing the object "bird" may correspond to the concept of "animal," in which case the concept is at a higher level of abstraction as the perception. This is an example in which the concept represents a class to which the corresponding perception belongs. The same perception may be mapped to multiple concepts at different levels of abstraction. For example, the perception "bird" may be mapped to the concepts "bird," "animal," and "physical object." Conversely, the same concept may be mapped to multiple perceptions. For example, the concept of "bird" may be mapped to the perceptions of "cardinal," "sparrow," and "swan." In this example, the concept (class) of "bird" is mapped to perceptions representing members (instances) of the class of "bird."

Once the induction module 504 has developed a knowledgebase containing two-way mappings between the perceptions in the perceptual memory 501 and the concepts in the conceptual memory 502, knowledge stored in the knowledgebase may be retrieved in any of a variety of ways. For example, the system includes a deduction module 505 which may retrieve knowledge from the knowledgebase using deduction. In particular, if data representing a perception in the perceptual memory 501 is provided as input to the deduction module 505, then the deduction module 505 may follow the mapping(s) from the perception in the perceptual memory 501 to the corresponding concepts(s) in the conceptual memory 502, and thereby retrieve the concept(s) that correspond to the perception. For example, if the perception "bird" is provided an input to the deduction module 505, then the deduction module 505 may follow the mapping from the perception "bird" in the perceptual memory 501 to the corresponding concept of "animal" in the conceptual memory 502 and return that concept, thereby indicating that the perception "bird" is a member of the class "animal."

As another example, the system includes a reduction module 506 which may retrieve knowledge from the knowledgebase using reduction. In particular, if data representing a class in the conceptual memory 502 is provided as input to the reduction module 506, then the reduction module 506 may follow the mapping(s) from the concept in the conceptual memory 502 to the corresponding perception(s) in the perceptual memory 501, and thereby retrieve the perception(s) that correspond to the concept. For example, if the concept "animal" is provided an input to the reduction module 506, then the reduction module 506 may follow the mapping from the concept "animal" in the conceptual memory 502 to the corresponding perceptions of "bird," "canine," and "feline" in the perceptual memory 501 and return those perceptions, thereby indicating that the perceptions "bird," "canine," and "feline" are members of the class "animal."

As can be seen from the description above, the system of FIG. 5, which includes the perceptual memory 501, the conceptual memory 502, and the mappings between them, provides a knowledgebase with a hierarchical structure. In particular, the two-way mappings between perceptions in the perceptual memory 501 and concepts in the conceptual memory 502 represent knowledge having a hierarchical structure, in which perceptions are members of classes, and in which classes are members of higher-level classes, and so on to any level of abstraction. For example, the system of FIG. 5 may represent a hierarchical relationship in which the perception of "cardinal" is mapped to the class of "bird," which in turn is mapped to a perception of "bird," which in turn is mapped to the class of "animal," and so on.

The system of FIG. 5 may be implemented in any of a variety of ways. For example, the system of FIG. 5 may represent perceptions, concepts, and the relationships (mappings) between them in any of a variety of ways. In particular, in certain embodiments disclosed herein, the perceptions in the perceptual memory 501 and the conceptions in the conceptual memory 502 are represented as binary numbers. For example, in certain embodiments of the present invention, a first sequence (such as a first protein sequence) is represented as a first binary number and a second sequence (such as a second protein sequence) is represented as a second binary number. Each such binary number may be divided into subsets representing perceptions and conceptions, and the techniques described above may be applied to store representations of such perceptions in the perceptual memory 501 and to store representations of such conceptions in the conceptual memory 502. The techniques described above may then be used to generate (learn) the relationships (mappings) between the perceptions and concepts for each such binary number. The resulting mappings may be stored in the knowledgebase of FIG. 5. The two sequences (represented as binary numbers) may be aligned with each other by comparing the mappings (knowledge) that have been learned and stored for the two sequences in the knowledgebase of FIG. 5. Particular examples of techniques for performing such alignment will now be described in more detail.

A sequence may be represented, for example, as a text string (e.g., the text string "GTCA" or the text string "11011"). Therefore, the terms "sequence" and "string" may be used interchangeably herein, although it should be understood that a string is an ordered set of characters that represents a sequence. Furthermore, terms such as "string" and "text string" should be understood to refer not only to sets of characters but to sets containing symbols other than characters.

In general, embodiments of the present invention may be used to align two binary numbers by considering each binary number to consist of 3-bit sequences. Embodiments of the present invention may represent binary numbers using the conventional representation, in which each bit has a range of $\{+1, 0\}$. However, alternatively, and in the following description, embodiments of the present invention may represent binary numbers with a range of {+1, −1}. In other words, in embodiments of the present invention, a binary number may have a value of either +1 (also written simply as 1) or −1. For example, the binary value 10011010 may be represented alternatively according to embodiments of the present invention as the value +1−1−1+1+1−1−1+1−1. This alternative representation, which is based on the primitive values of +1 and −1, is advantageous over the conventional use of the primitive values of +1 and 0, because the +1 and −1 are both equal in magnitude to each other (because they both have an absolute value or magnitude of 1) but opposite in direction to each other (because +1 has a positive direction and −1 has an opposite, negative direction). In contrast, the conventional binary values of +1 and 0 are neither equal in magnitude to each other nor opposite in direction to each other. (In fact, the value of 0 does not have a magnitude or direction.)

As described in more detail in the above-referenced patent application entitled, "Spatial Arithmetic Method of Integer Factorization," the use of +1 and −1 as primitive values enables numbers represented as combinations of +1 and −1 to be represented as three-dimensional points in a three-dimensional space more easily and directly than numbers represented as combinations of +1 and 0. This further facilitates use of such numbers to perform arithmetic (such as multiplication, division, addition, or subtraction), factorization, and other operations more easily than conventional binary numbers composed of primitive values of 0 and 1.

Because the use of +1 and −1 to represent numbers is new, there is no existing terminology to refer to a number which has permissible values consisting of the set {+1, −1}. The existing term "bit" refers to a number which has a range of permissible values consisting of the set {+1, 0}. For ease of explanation, and because embodiments of the present invention may use either a representation based on {+1, 0} or {+1, −1}, the term "bit" will be used herein to refer both to numbers that have a range of permissible values consisting of the set {+1, 0} and to numbers that have a range of permissible values consisting of the set {+1, −1}. Similarly, the term "binary number" will be used herein to refer to any number consisting of bits, whether such bits have a range of {+1, 0} or {+1, −1}. For example, both the number 10011010 and the number +1−1−1+1+1−1+1−1 will be referred to herein as "binary numbers," even though the number +1−1−+1−1−+1+1−1+1−1 does not contain "bits" in the conventional sense.

For example, the binary number +1−1+1+1+1−1−1+1+1 may be considered to consist of the three 3-bit sequences +1−1+1, +1+1−1−, and −1+1+1. The significance of the length of three will be described in more detail below. A binary number that has a number of bits that is not an integral multiple of three may be considered to have a number of leading −1s that is sufficient to make the number have a number of bits that is an integral multiple of three. For example, the binary number −1+1+1−1, which has four bits, may be considered to be have two leading −1s, i.e., −1−1−1+1+1−1, which consists of the two 3-bit sequences −1−1−1 and +1+1−1. Therefore, when an embodiment of the presented invention is presented with a binary number to align that has a number of bits that is not an integral multiple of three, the embodiment may append a number of leading −1s to the number sufficient to make the length of the number an integral multiple of three.

A binary number that has been mapped to three dimensions in the manner disclosed herein may be represented as a sequence of relations in a three-dimensional space. For example, referring to FIG. 6A, a three-dimensional space 600 is shown having three dimensions representing orthogonal axes in a three-dimensional space. In particular, the x dimension may represent an x axis in the three-dimensional space 600, the y dimension may represent a y axis in the three-dimensional space 600, and the z dimension may represent a z axis in the three-dimensional space 600, where the x, y, and z axes are orthogonal to each other.

Figure 6A:
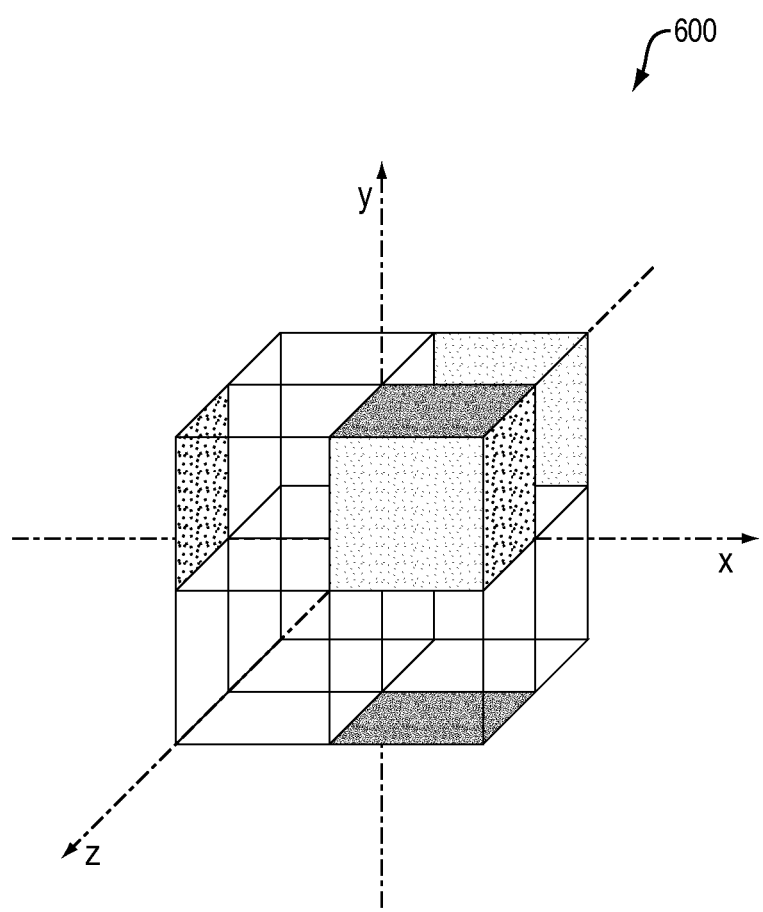
FIG. 6A illustrates a three-dimensional space which may be used to represent numbers according to embodiments of the present invention.

FIG. 6A shows a cube consisting of eight points in the three-dimensional space, namely the points (−1, −1, −1), (−1, −1, +1), (−1, +1, −1), (−1, +1, +1), (+1, −1, −1), (+1, −1, +1), (+1, +1, −1), and (+1, +1, +1). These eight points represent the "core" layer. The shaded cube in FIG. 6A is located at coordinates (+1, +1, +1) in the three-dimensional space 600.

According to embodiments of the present invention, the three-dimensional space 600 may have a layered coordinate system, and each number may be represented as a collection of points in the three-dimensional space 600. Each number may include one or more layers within the coordinate system of the three-dimensional space 600. For any particular number, each layer corresponds to a particular bit position within the number, and each number is read from the outside layer to the inside layer. Each number is represented as a combination of bits (which, as stated above, may have a value of +1 or −1). The bits of each number are ordered within the three dimensions of the three-dimensional space 600. The values of +1 and −1 represent opposite directions in the three-dimensional space 600.

Figure 6D:
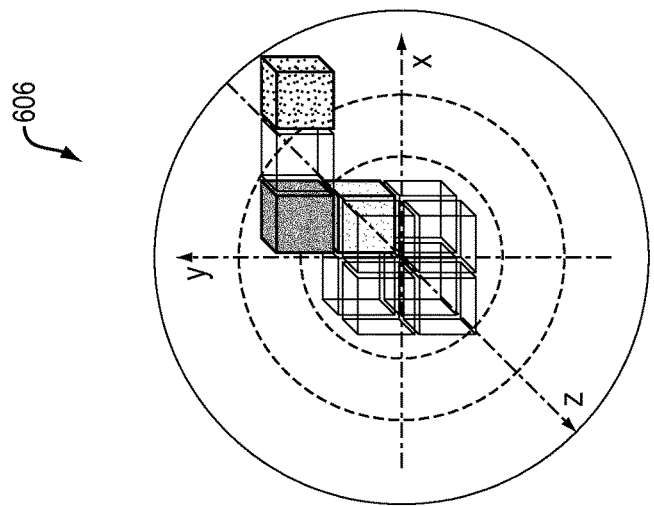
FIGS. 6B, 6C, and 6D illustrate three-dimensional representations of the numbers 1, 2, and 3 according to embodiments of the present invention.
Figure 6C:
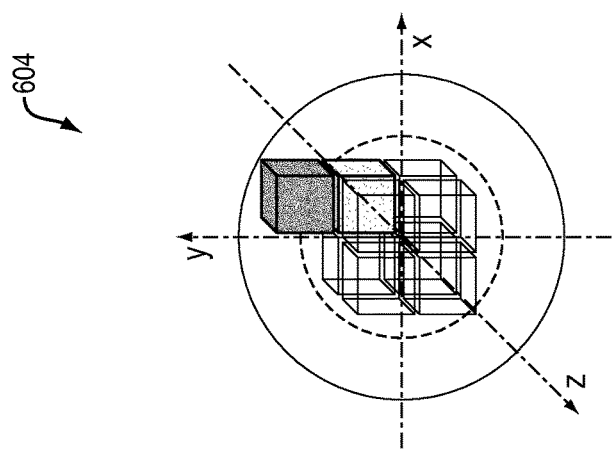
Figure 6B:
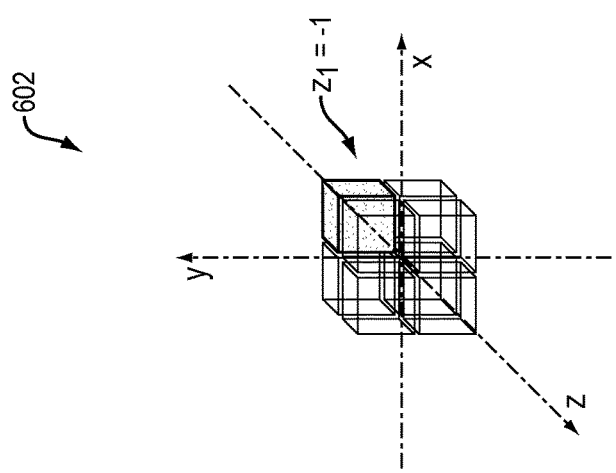

FIGS. 6B, 6C, and 6D illustrate layered relations between the coordinates. To illustrate the layers, consider the decimal number six, which may be represented as the binary number +1+1−1. If we assume the three dimensions the order of z, y, x, then this number may be mapped to the three dimensions as follows: $+1x_3+1y_2-1z_1$. The first, "core" layer 602 shown in FIG. 6B contains the same set of eight three-dimensional points as shown in FIG. 6A. The first bit ($-1z_1$) is illustrated in FIG. 6B by a point having a z coordinate at z=−1. This is the first layer of the binary number +1+1−1.

FIG. 6C illustrates the second layer 604, which extends along the direction of the y axis. The second bit ($+1y_2$) in the binary number +1+1−1 is illustrated in FIG. 6C by a point having a y coordinate at y=2, namely the point in FIG. 6C at (1, 2, −1). Note that this point was not present in the first layer 602 of FIG. 6A, but was added to the first layer 602 of FIG. 6B to produce the second layer 604 of FIG. 6C. As illustrated by this example, in which the second layer 604 contains the entirety of the previous (first) layer 602 plus one or more additional points extending along the y axis, each new layer contains the entirety of the previous layer plus one or more additional points extending along the axis corresponding to the new layer.

FIG. 6D illustrates the third layer 606, which extends along the direction of the x axis. The third bit ($+1x_3$) in the binary number +1+1−1 is illustrated in FIG. 6D by a point having an x coordinate at x=3, namely the point in FIG. 6D at (3, 2, −1), which was not present in the second layer 604 of FIG. 6C, and which was added to the second layer 604 of FIG. 6C to produce the third layer 606 of FIG. 6D. (The unfilled point at (2, 2, −1) represents a coordinate relation between the point at (3, 2, −1) in the third layer and the point at (1, 2, −1) in the second layer.)

Figure 6E:
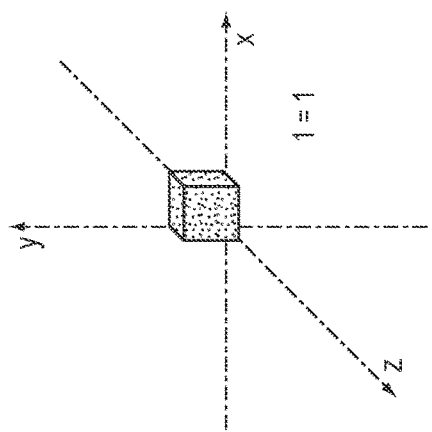
FIGS. 6E-6H illustrate three-dimensional representations of the origin point and various numbers according to embodiments of the present invention.
Figure 6F:
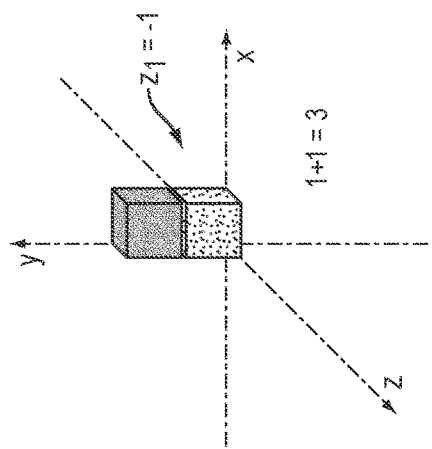

Embodiments of the present invention may be used to represent numbers according to layers such as those shown in FIGS. 6B-6D. To understand how to represent numbers according to the layers of FIGS. 6B-6D, consider FIGS. 6E-6H. First, consider the origin point at (0, 0, 0), illustrated in FIG. 6E. This point represents the number zero.

Now consider the binary number 1. To construct a three-dimensional representation of this number, assume that the order of the dimensions is x, y, z. The three-dimensional representation of the binary number 1 is constructed by reading each bit in the number and creating a point in three-dimensional space corresponding to that bit, to create a set of three-dimensional points corresponding to the number. Because the binary number 1 only contains 1 bit, the corresponding representation of the binary number 1 in three-dimensional space consists of exactly one point in three-dimensional space, namely a single point corresponding to the bit 1.

More specifically, the number to be represented in three-dimensional space is read one bit at a time, starting with the lowest bit on the right and moving toward the highest bit on the left in sequence to the next highest bit until the highest bit in the number is reached. A corresponding point in three dimensional space is created for each such bit.

Recall that the three dimensions are assigned a particular order. Assume for purposes of example that the dimensions are assigned an order of x, y, z. Therefore, the first (lowest) bit in a number is associated with the x dimension, the second (next-lowest) bit in the number is associated with the y dimension, the third (next-lowest) bit in any number is associated with the z dimension, the fourth (next-lowest) bit in any number is associated with the x dimension, and so on. In other words, the bits in the number are assigned to the x, y, and z dimensions in a repeating pattern (in whatever order has been assigned to the x, y, and z dimensions), starting with the lowest bit of the number and continuing bit-by-bit until the highest bit of the number is reached.

Each dimension is associated with a corresponding number, starting with 1, and increasing incrementally, in a repeating pattern of dimensions. For example, if the dimensions are assigned the order x, y, z, then the number 1 may be associated with the x dimension 1, the number 2 may be associated with the dimension y, the number 3 may be associated with the dimension z, the number 4 may be assigned to the dimension x, and so on. As this example illustrates, each dimension may be associated with more than one number, depending on the corresponding bit position. Each bit position may be designated with a subscript after the corresponding dimension, such as $x_1$, $y_2$, $z_3$, $x_4$, $y_5$, $z_6$, etc. The assignment of bits in a binary number may be designated by writing each bit followed by its associated dimension. For example, the binary number +1−1+1+1+1−1 may be written as $+1x_1 -1y_2 +1z_3 +1x_4 +1y_5 -1z_6$.

Techniques that may be used to represent binary numbers in three-dimensional space according to embodiments of the present invention will now be described. First consider the decimal number 1, which is equal to the binary number 1. The lowest bit of this number is assigned to the first dimension in the assigned order of dimensions. In this case, the lowest bit is equal to 1, and the first dimension is the x dimension. Therefore the value of 1 is assigned to the x dimension. As described above, this may be written as $+1x_1$.

A point representing $+1x_1$ may then be created in three-dimensional space to represent the first bit of the binary number 1. A point representing $+1x_1$ (which may alternatively be written as $x_1$) may be created by starting at the origin point and moving along the axis indicated by $+1x_1$ (namely, the x axis), in the direction indicated by $+1x_1$ (namely, in the positive direction), to the coordinate on the x axis indicated by the subscript of $+1x_1$ (namely, to the coordinate x=0). This results in the creation of a point at $x_1=1$, $y_1=1$, $z_1=1$. This single point represents the binary number 1. Note that coordinates of x=0, y=0, and z=0 are only used to represent the number 0, namely by the origin at (0, 0, 0). No other number is represented by a point having any coordinate equal to zero.

Now consider the decimal number 2, which is equal to the conventional binary number 10 and to the binary number +1−1 according to certain embodiments of the present invention. These two bits, starting with the lowest bit and moving bit-by-bit to the highest bit, may be assigned to the x and y dimensions, respectively. For example, the binary number +1−1 may be assigned to the x and y dimensions to produce a mapping of the binary number +1−1 to the representation $+1y_2 -1x_1$.

Figure 6G:
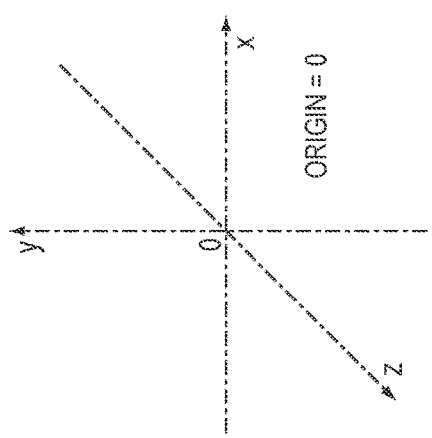

Based on this assignment of bits to dimensions, and as shown in FIG. 6G, the binary number +1−1 may be represented in three-dimensional space by a collection of points, each of which corresponds to a corresponding bit in the binary number +1−1. In particular, because the binary number +1−1 contains exactly two bits, the binary number +1−1 is represented by exactly two points in three-dimensional space in FIG. 6G. More specifically, reading from the lowest bit to the highest bit:

the lowest bit in $+1y_2 -1x_1$ (i.e., the rightmost bit, having a value of $-1x_1$), is represented by a point at x=−1, y=1, z=1;

the next-lowest bit in $+1y_2 -1x_1$ (i.e., the leftmost bit, having a value of $+1y_2$), is represented by a point at x=−1, y=2, z=1, as the result of moving from the previous point (x=−1, y=1, z=1) in the positive direction on the y axis to the coordinate y=2.

The resulting three-dimensional representation of decimal 2 is, as shown in FIG. 6G, a set of exactly two points at coordinates (x=−1, y=1, z=1) and (x=−1, y=2, z=1). Note that in the case of a one-bit or two-bit number, the z coordinates (or more generally, the coordinates of the third dimension in the ordered sequence of dimensions) may be chosen arbitrarily because the z (third) coordinate is not necessary to represent the number.

Now consider the decimal number 3, which is equal to the conventional binary number 11 and to the binary number +1+1 according to certain embodiments of the present invention. These two bits, starting with the lowest bit and moving bit-by-bit to the highest bit, may be assigned to the x, y, and z dimensions. As a result, the binary number +1+1 may be assigned to the x, y, and z dimensions to produce $+1y_2 +1x_1$.

Figure 6H:
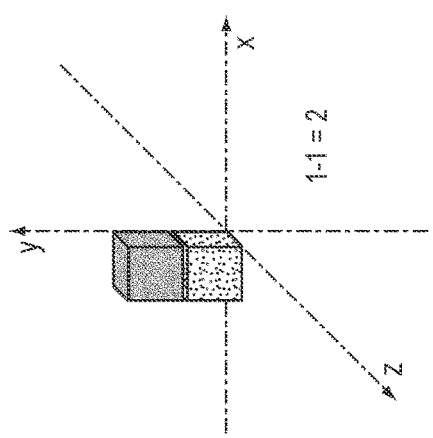

Based on this assignment of bits to dimensions, and as shown in FIG. 6H, the binary number +1+1 may be represented in three-dimensional space by a collection of points, each of which corresponds to a corresponding bit in the binary number +1+1. In particular, because the binary number +1+1 contains exactly two bits, the binary number +1+1 is represented by exactly two points in three-dimensional space in FIG. 6H. More specifically, reading from the lowest bit to the highest bit:

the lowest bit in $+1y_2 +1x_1$ (i.e., the rightmost bit, having a value of $+1x_1$), is represented by a point at x=1, y=1, z=1;

the next-lowest bit in $+1y_2 +1x_1$ (i.e., the leftmost bit, having a value of $+1y_2$), is represented by a point at x=1, y=2, z=1, as the result of moving from the previous point (x=1, y=1, z=1) in the positive direction on the y axis to the coordinate y=2.

The resulting three-dimensional representation of decimal 3 is, as shown in FIG. 6H, a set of exactly two points at coordinates (x=+1, y=1, z=1) and (x=1, y=2, z=1).

Those having ordinary skill in the art will appreciate how to use the techniques disclosed above to create three-dimensional representations of any decimal number, whether negative or positive. Further examples of such representations are shown and described in the above-referenced patent application entitled, "Spatial Arithmetic Method of Integer Factorization."

In general, to align two binary numbers with each other, embodiments of the present invention divide each such number into 3-bit sequences, and then align the corresponding 3-bit sequences in the two numbers with each other. Because each such pair of 3-bit sequences may be aligned in a fixed amount of time, the two binary numbers may be aligned with each other in an amount of time that is a polynomial function of the length of the longer of the two numbers. As a result, the amount of time required to align two numbers (sequences) when using embodiments of the present invention grows only as a polynomial function of the length of the longer of the two numbers. This represents a significant decrease in time compared to conventional alignment methods, which align numbers (sequences) in an amount of time that is an exponential function of the length of the longer of the two numbers.

A three-dimensional representation of each of the two binary numbers to be aligned with each other may be created in accordance with the description above and FIGS. 6A-6H. The process of aligning the two binary numbers with each other may take into account both the values of the bits in each number (e.g., +1 or −1) and the three-dimensional position of each bit. In other words, the two binary numbers may be aligned with each other based, in whole or in part, on the three-dimensional representations of those numbers. The use of the three-dimensional positions of bits to align two numbers will be explained in more detail below.

Before describing how to perform alignment of binary numbers according to embodiments of the present invention in more detail, techniques that may be used to represent binary numbers as perceptions, concepts, and the relationships between them in the system of FIG. 5 will be described. Referring to FIG. 1, an example is shown of a particular string 100 that may represent a sequence (such as a protein sequence). The particular string 100 shown in FIG. 1 is merely an example and does not constitute a limitation of the present invention. For example, the length of the string 100 shown in FIG. 1 is merely an example. Embodiments of the present invention may be applied to strings of any length. As another example, although the particular string 100 shown in FIG. 1 consists of bits, this is merely an example and does not constitute a limitation of the present invention. Embodiments of the present invention may be used in connection with strings containing symbols of any kind.

The string 100 shown in FIG. 1 contains five bits 102a-e, namely bit 102a (having a value of +1), bit 102b (having a value of +1), bit 102c (having a value of −1), bit 102d (having a value of +1) and bit 102e (having a value of +1). This particular combination of symbols is merely an example and does not constitute a limitation of the present invention, which may be used in connection with strings containing any combination of symbols.

According to embodiments of the present invention, a string, such as the string 100 shown in FIG. 1, may be divided (i.e., decomposed) into or otherwise associated with a plurality of sub-strings. FIG. 1 shows one possible way in which the string 100 may be divided into and associated with a plurality of sub-strings. The particular example in FIG. 1 is shown merely for ease of illustration and does not constitute a limitation of the present invention. Rather, as will be described in more detail below, strings (such as the string 100) may be divided into multiple sub-strings in any of a variety of ways.

For example, as shown in FIG. 1, the string 100 may be divided into individual symbols 102a-e in a first layer 104a. In other words, layer 104a contains a plurality of elements, each of which consists of a single symbol from the string 100. More specifically, the layer 104a consists of each individual symbol from the string 100, namely symbol 102a, symbol 102b, symbol 102c, symbol 102d, and symbol 102e. Each individual symbol in the first layer 104a may also be referred to herein as a "literal." Therefore the first layer 104a may be referred to herein as the "literal layer."

As further shown in FIG. 1, the string 100 may be divided into sets of symbols in a second layer 104b, where each set in the layer 104b contains exactly two consecutive symbols from the string 100, and wherein the layer 104b contains all sets of two consecutive symbols from the string 100. More specifically, layer 104b consists of: (1) symbol set 106a, which consists of the first consecutive set of two symbols 102a-b from the string 100; (2) symbol set 106b, which consists of the second consecutive set of two symbols 102b-c from the string 100; (3) symbol set 106c, which consists of the third consecutive set of two symbols 102c-d from the string 100; and (4) symbol set 106d, which consists of the fourth consecutive set of two symbols 102d-e from the string 100. Each set of two symbols in the second layer 104b (e.g., the sets 106a-d) may also be referred to herein as a "word." Therefore, the second layer 104b may be referred to herein as the "word layer."

As further shown in FIG. 1, the string 100 may be divided into sets of symbols in a third layer 104c, where each set in the layer 104c contains exactly three consecutive symbols from the string 100, and wherein the layer 104c contains all sets of three consecutive symbols from the string 100. More specifically, layer 104c consists of: (1) symbol set 108a, which consists of the first consecutive set of three symbols 102a-c from the string 100; (2) symbol set 108b, which consists of the second consecutive set of three symbols 102b-d from the string 100; and (3) symbol set 108c, which consists of the third consecutive set of three symbols 102c-e from the string 100 Each set of three symbols in the third layer 104c (e.g., the sets 108a-c) may also be referred to herein as a "clause." Therefore, the third layer 104c may be referred to herein as the "clause layer."

The string 100 shown in FIG. 1 may also be divided into sub-strings each containing more than three literals, such as sub-strings each containing four literals, five literals, or six literals. Any such sub-strings, containing four or more literals each, are referred to herein as "sentences." As will be described in more detail below, embodiments of the present invention may, but need not, divide strings into sentences. Rather, embodiments of the present invention need only identify the literals, words, and clauses that constitute a string. The processing described herein, in other words, may be performed on sub-strings containing no more than three literals each. As will further be described in more detail below, embodiments of the present invention that perform processing on clauses (possibly in addition to literals and words) have advantages over techniques that perform processing only on literals, words, or combinations of literals and words, because of particular benefits conveyed by the use of clauses (i.e., sub-strings containing exactly three literals each).

As may be seen from the example of FIG. 1, for each layer i (where i=1 for layer 104a, i=2 for layer 104b, and i=3 for layer 104c): (1) each set in layer i contains exactly i symbols; and (2) the number of sets in layer i is equal to n−i+1, where n is the number of symbols in the string 100.

It should also be appreciated that although the discussion above refers to "dividing" the string 100 into sub-strings within the levels 104a-c, such division (i.e., decomposition) need not be implemented by actually dividing the string 100 into sub-strings, or by copying symbols within the strings into sub-strings to create separate sets of symbols corresponding to the illustration in FIG. 1. Rather, FIG. 1 is intended as a conceptual illustration of associations that may be identified by embodiments of the present invention between the string 100 and sets of symbols representing subsets of the string 100. In practice, such associations may be represented (e.g., by data structures created and/or manipulated by a computer program) with or without copying symbols within the string 100. For example, associations of the kind illustrated in FIG. 1 may be represented using pointers, linked lists, array indices, or any other suitable kinds of data structure, as will be apparent to those having ordinary skill in the art based on the description herein.

FIG. 1 also illustrates relationships between the various levels 104a-c. For example, FIG. 1 illustrates relationships 112a-h between levels 104a and 104b. More specifically, these relationships 112a-h include:

relationship 112a between literal 102a in level 104a and literal 102a in word 106a of level 104b;
relationship 112b between literal 102b in level 104a and literal 102b in word 106a of level 104b;
relationship 112c between literal 102b in level 104a and literal 102b in word 106b of level 104b;
relationship 112d between literal 102c in level 104a and literal 102c in word 106b of level 104b;
relationship 112d between literal 102c in level 104a and literal 102c in word 106b of level 104b;
relationship 112e between literal 102c in level 104a and literal 102c in word 106c of level 104b;
relationship 112f between literal 102d in level 104a and literal 102d in word 106c of level 104b;
relationship 112g between literal 102d in level 104a and literal 102d in word 106d of level 104b; and
relationship 112h between literal 102e in level 104a and literal 102e in word 106d of level 104b.

Note that the relationships 112a-h form a "sawtooth" pattern between levels 104a and 104b. This sawtooth pattern results from the overlap of literals between successive words in level 104b. For example:

Words 106a and 106b overlap at literal 102b. This is reflected by relationships 112b and 112c, which connect words 106a and 106b in level 104b to the overlapping literal 102b in level 104a.
Words 106b and 106c overlap at literal 102c. This is reflected by relationships 112d and 112e, which connect words 106b and 106c in level 104b to the overlapping literal 102c in level 104a.
Words 106c and 106d overlap at literal 102d. This is reflected by relationships 112f and 112g, which connect words 106c and 106d in level 104b to the overlapping literal 102d in level 104a.

Furthermore, FIG. 1 illustrates relationships 114a-f between levels 104b and 104c. More specifically, these relationships 114a-f include:

relationship 114a between word 106a in level 104b and word 106a in clause 108a of level 104c;
relationship 114b between word 106b in level 104b and word 106b in clause 108a of level 104c;
relationship 114c between word 106b in level 104b and word 106b in clause 108b of level 104c;
relationship 114d between word 106c in level 104b and word 106c in clause 108b of level 104c;
relationship 114e between word 106c in level 104b and word 106c in clause 108c of level 104c; and
relationship 114f between word 106d in level 104b and word 106d in clause 108c of level 104c.

Note that the relationships 114a-f form a "sawtooth" pattern between levels 104b and 104c. This sawtooth pattern results from the overlap of words between successive clauses in level 104c. For example:

Clauses 108a and 108b overlap at word 106b. This is reflected by relationships 114b and 114c, which connect clauses 108a and 108b in level 104c to the overlapping word 106b in level 104b.
Clauses 108b and 108c overlap at word 106c. This is reflected by relationships 114d and 114e, which connect clauses 108b and 108c in level 104c to the overlapping word 106c in level 104b.

The totality of the relationships illustrated in FIG. 1 provide one example of the reason that embodiments of the present invention use data elements each containing at least three literals (i.e., clauses), and of the reason that embodiments of the present invention are not required to use data elements each containing more than three literals. In general, embodiments of the present invention may be used to process knowledge that represents reciprocal relations between physical (also referred to herein as "perceptual") data and conceptual data, as described in more detail in the above-referenced U.S. Pat. No. 6,611,841. Although a literal (i.e., a single bit) may encode a unit of information, it is insufficient to encode a relation between two units of information. A word (i.e., two bits) may encode a relation between two units of information. A mere collection of words can represent a collection of distinct relations between literals. A word, however, cannot represent a relation between relations because the constituent elements of a word are literals, which themselves do not represent relations.

To represent a relation between two relations requires at least the use of a clause (i.e., three bits). For example, as illustrated by FIG. 1, it is only at level 104c, which contains clauses, that it becomes possible to represent relations between relations, i.e., relations between words, where each word represents a relation between literals. For example, the clause 108a in level 104c represents a relation between words 106a and 106b, as reflected in the overlap of words 106a and 106b at literal 102b within clause 108a.

Relations between relations may further be represented by sentences of any length (e.g., length 4, 5, 6, or greater). For example, a sentence of length 4 may represent a relation between two clauses of length 3. The minimum length required to represent a relation between relations, however, is 3. If data elements consisting of at least clauses are used, a knowledge acquisition and retrieval system that represents reciprocal relations between physical (i.e. perceptual) data and conceptual data, of the kind disclosed in U.S. Pat. No. 6,611,841, may be implemented using such data elements to represent such reciprocal relations. In the example of FIG. 1, the elements 102a-e in layer 104a are an example of perceptual data, while the elements 108a-c in layer 104c are an example of conceptual data in relation to the perceptual data of layer 104a. More generally, the representation of FIG. 1 moves from perceptual data to conceptual data as the layers 104a-c are followed downward in FIG. 1.

The symbols and relationships shown in FIG. 1 are examples of what are shown in FIG. 5 as perceptions in the perceptual memory 501, concepts in the conceptual memory 502, and relationships (mappings) between the perceptions and concepts in the induction module 504. For example:
- bits 102a-e in layer 104a are examples of perceptions in the perceptual memory 501 of FIG. 5;
- symbol sets 106a-106d are examples of concepts in the conceptual memory 502 of FIG. 5; and
- relationships 112a-h are examples of relationships (mappings) between perceptions and conceptions in the induction module 504 of FIG. 5.

As mentioned above, concepts in the conceptual memory 502 may also be perceptions in the perceptual memory 501. For example:
- symbol sets 106a-d are examples of perceptions in the perceptual memory 501 of FIG. 5;
- symbol sets 108a-c are examples of concepts in the conceptual memory 502 of FIG. 5; and
- relationships 114a-f are examples of relationships (mappings) between perceptions and conceptions in the induction module 504 of FIG. 5.

Figure 2A:
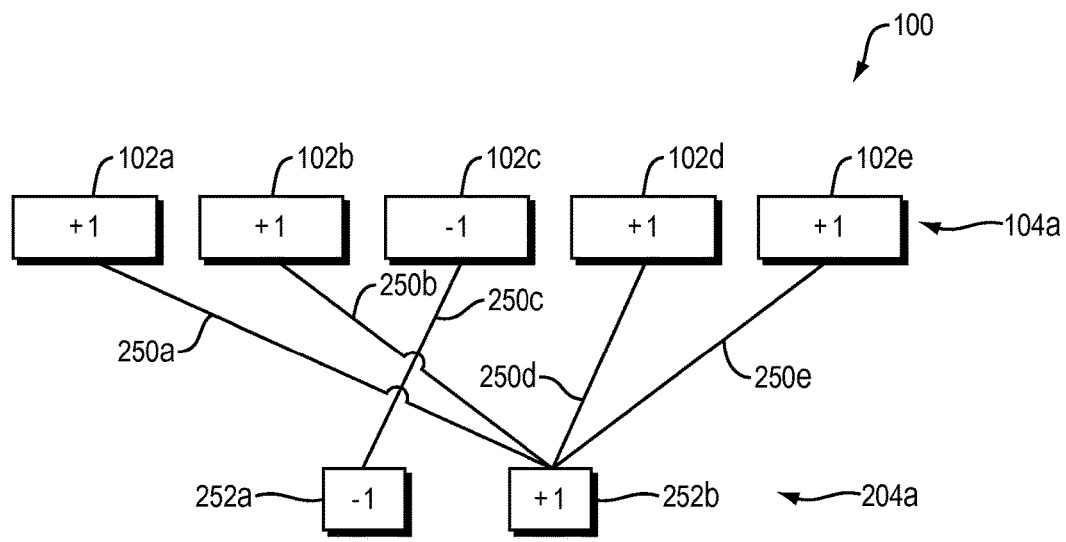
FIG. 2A is a diagram illustrating bidirectional mappings between the string of FIG. 1 and a literals layer.
Figure 2B:
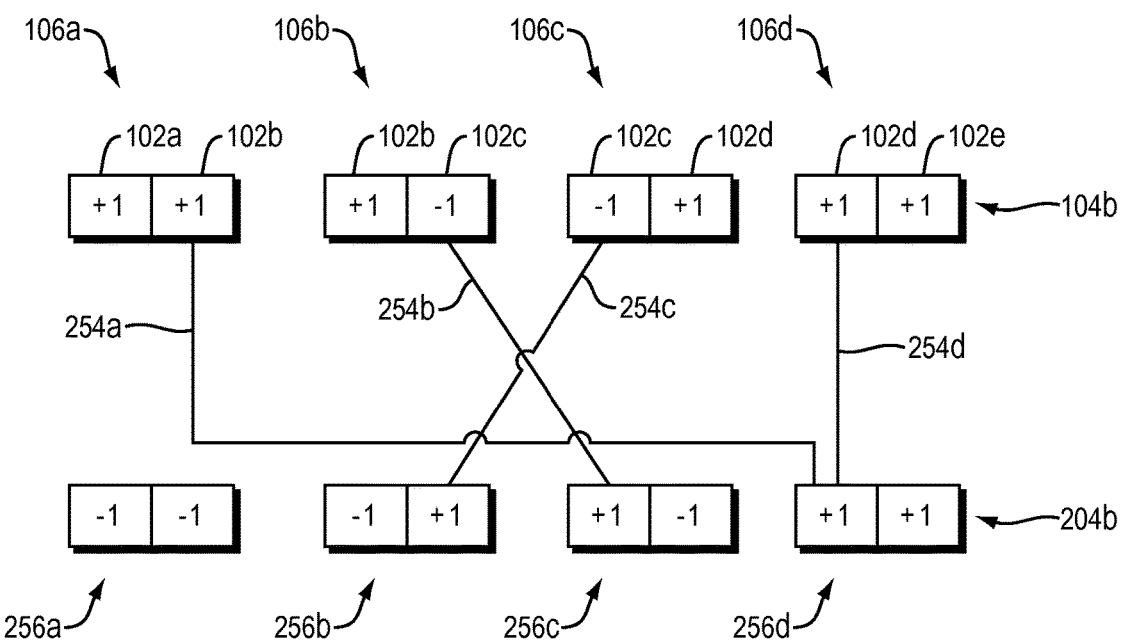
FIG. 2B is a diagram illustrating bidirectional mappings between the string of FIG. 1 and a words layer.
Figure 2C:
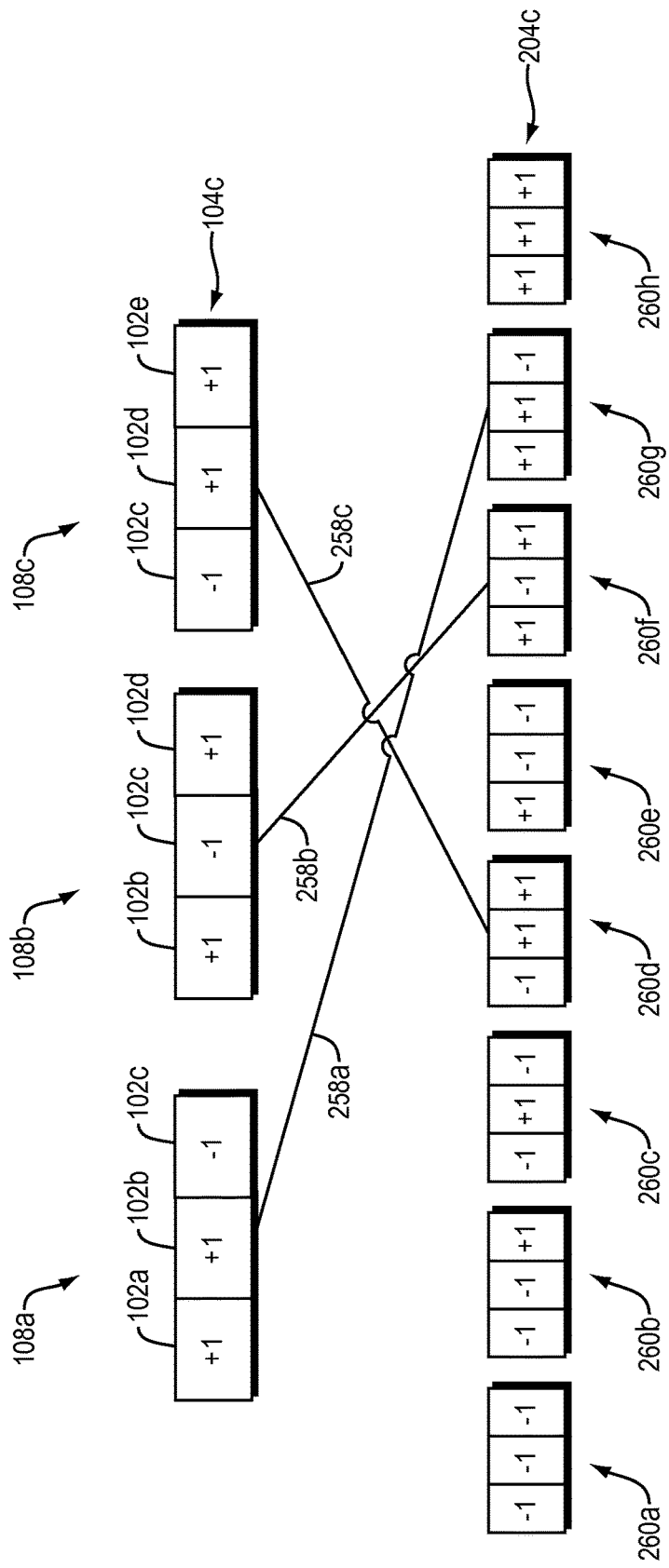
FIG. 2C is a diagram illustrating bidirectional mappings between the string of FIG. 1 and a clauses layer.

Referring to FIGS. 2A-2C, an alternative illustration is shown of associations between the string 100 and subsets of the string 100. Although conceptually FIG. 2 represents the same information as FIG. 1, FIG. 2 illustrates that information in a different form, in which the string 100 is associated with (i.e., mapped to) symbol sets within multiple layers.

Referring to FIG. 2A, string 100 is shown with a first layer 204a. The first layer 204a is another example of a literals layer. First layer 204a contains individual symbols 252a and 252b, which in this example are individual bits. In FIG. 2A, the first layer 204a contains all symbols in the symbol set from which the symbols in the string 100 were selected. In the example of FIG. 2A, the string 100 is a set of binary numbers (i.e., bits), so the first layer 204a contains all individual binary symbols, namely −1 252a and +1 252b.

Embodiments of the present invention may map each of the symbols in the string 100 to an element (e.g., bit) in the first layer 204a that contains the same symbol. In the particular example of FIG. 2A, this has resulted in the following mappings:
- mapping 250a of symbol 102a to element 252b;
- mapping 250b of symbol 102b to element 252b;
- mapping 250c of symbol 102c to element 252a;
- mapping 250d of symbol 102d to element 252b; and
- mapping 250e of symbol 102d to element 252b.

Similarly, embodiments of the present invention may map subsets (e.g., substrings) of the string 100 to elements (e.g., symbol sets) in other layers. For example, referring to FIG. 2B, the symbol sets 106a-d from the second layer 104b of FIG. 1 are shown. FIG. 2B illustrates mappings 254a-d between the symbol sets 106a-d and 256a-d in a second layer 204b.

The second layer 204b is another example of a word layer. Second layer 204b contains symbol sets 256a-d, of which is a word in this example. In FIG. 2B, the second layer 204b contains all symbol sets containing combinations of two symbols from the symbol set from which the symbols in the string 100 were selected. In the example of FIG. 2B, the string 100 is a set of binary numbers (i.e., bits), so the second layer 204b contains all combinations of two binary symbols, namely −1−1 (set 256a), −1+1 (set 256b), +1−1 (set 256c), and +1+1 (set 256d).

Embodiments of the present invention may map each of the words in the string 100 to an element (e.g., word) having the same value (e.g., word) in the second layer 204b. In the particular example of FIG. 2B, this has resulted in the following mappings:
- mapping 254a of word 106a to element 256d;
- mapping 254b of word 106b to element 256c;
- mapping 254c of word 106c to element 256b; and
- mapping 254d of word 106d to element 256d.

As another example, referring to FIG. 2C, the symbol sets 108a-c from the third layer 104c of FIG. 1 are shown. FIG. 2C illustrates mappings 258a-c between the symbol sets 108a-c and clauses 260a-h in a third layer 204c.

The third layer 204c is another example of a clause layer. Third layer 204c contains symbol sets 260a-h, of which is a clause in this example. In FIG. 2C, the third layer 204c contains all symbol sets containing combinations of three symbols from the symbol set from which the symbols in the string 100 were selected. In the example of FIG. 2C, the string 100 is a set of binary numbers (i.e., bits), so the third layer 204c contains all combinations of three binary symbols, namely −1−1−1 (set 260a), −1−1+1 (set 260b), −1+1−1 (set 260c), −1+1+1 (set 260d), +1−1−1 (set 260e), +1−1+1 (set 260f), +1+1−1 (set 260g), and +1+1+1 (set 260h).

Embodiments of the present invention may map each of the clauses in the string 100 to an element (e.g., clause) having the same value (e.g., clause) in the third layer 204c. In the particular example of FIG. 2C, this has resulted in the following mappings:
- mapping 258a of clause 108a to element 260g;
- mapping 258b of clause 108b to element 260f; and
- mapping 258c of clause 108c to element 260d.

It should be apparent from FIG. 1 and FIGS. 2A-2C that the division of the string 100 into sub-strings in FIG. 1 and the mappings between sub-strings of string 100 and various elements in FIGS. 2A-2C are equivalent to each other and represent the same information in different forms. Those having ordinary skill in the art will appreciate that FIG. 1 and FIGS. 2A-2C may be implemented in any of a variety of ways. For example, each of the various layers 204a-c is illustrated in FIGS. 2A-2C as containing all possible combinations of i symbols (where i is the layer index). This may, for example, be implemented by creating, for each layer i, data structures representing all possible combinations of i symbols. In practice, however, the effect of FIGS. 2A-2C may be achieved without creating all (or even any) of such data structures. For example, the effect of FIGS. 2A-2C may be achieved by creating only those data structures to which an element of the string 100 is mapped. For example, in the case of FIG. 2B, there are mappings to words 256b, 256c, and 256d in layer 204b, but there is no mapping to word 256a. Therefore, data structures representing words 256b, 256c, and 256d may be created and mapped to data structures representing symbol sets 106a-d of the string 100, but no data structure representing word 256a need be created.

Alternatively for example, FIGS. 1 and 2A-2C may be implemented by assigning distinct numerical values to the symbol sets within each of the layers 204a-C. For example, in the case of FIG. 2B, the decimal value 0 may be assigned to word 256a, the decimal value 1 may be assigned to word 256b, the decimal value 2 may be assigned to word 256c, and the decimal value 3 may be assigned to word 256d. In this case, the mapping 254a may be represented by associating the decimal value 3 with word 106a, the mapping 254b may be represented by associating the decimal value 2 with word 106b, the mapping 254c may be represented by associating the decimal value 1 with word 106c, and the mapping 254d may be represented by associating the decimal value 3 with word 106d. As this example illustrates mappings may be implemented without creating separate data structures representing elements in the layers 204a-c (such as symbol sets 256a-d in layer 204b).

The particular implementations described above are merely examples of ways in which to implement FIGS. 1 and 2A-2C. Those having ordinary skill in the art will understand, based on the description herein, how to implement FIGS. 1 and 2A-2C in other ways that fall within the scope of the present invention.

Although FIGS. 2A-2C are provided herein as separate illustrations of mappings between various subsets of string 100 and layers 204a, 204b, and 204c, in practice embodiments of the present invention may be used to create any one or more of the mappings illustrated in FIGS. 2A-2C.

In general, embodiments of the present invention may perform alignment of a first sequence with a second sequence by: (1) generating mappings between the first sequence and literals, words, and clauses formed from an alphabet, in the manner illustrated by FIGS. 1 and 2A-2C; (2) generating mappings between the second sequence and literals, words, and clauses formed from the alphabet, in the manner illustrated by FIGS. 1 and 2A-2C; and (3) aligning the first sequence with the second sequence by comparing the clauses of the first sequence with the clauses of the second sequence.

FIGS. 3A-3B and 4A-4B generally illustrate systems and methods that may be used to generate mappings between a string and one or more layers of the kind illustrated in FIG. 1 according to one embodiment of the present invention. First, the specific operation of FIGS. 3A-3B and 4A-4B will be described. Next, techniques for using the mappings generated by FIGS. 3A-3B and 4A-4B to perform sequence alignment will be described.

The system 300 (FIG. 3A) and method 400 (FIG. 4A) may operate as follows. The system 300 includes a string 302, such as the string 100 shown in FIG. 1. The system 300 also includes a string subset identification module 304. In general, the subset identification module 304 identifies, for each of a plurality of layers, a plurality of subsets of the string 302 within that layer. For example, the method 400 of FIG. 4A may enter a loop over each of a plurality of layers indices i (FIG. 4A, operation 402). The values of i may be selected from any set, such as $\{1, 2\}$, $\{1, 2, 3\}$, $\{1, 2, 3, 4\}$, $\{2, 3\}$, or $\{2, 3, 4\}$.

For each value of i, the subset identification module 304 may identify (e.g., generate) a plurality of subsets of the string 302 corresponding to layer i, wherein each subset in the plurality of subsets contains exactly i symbols (e.g., i consecutive symbols) from the string (FIG. 4A, operation 404). The subset identification module 304 may, for example, identify all distinct subsets of the string 302 that consist of consecutive symbols from the string and that contain exactly i symbols. The subsets 102a-e, 106a-d, 108a-c, and 110a-b shown in FIG. 1 are examples of such subsets.

The subset identification module 304 may repeat operation 404 for the remaining layers (FIG. 4A, operation 406). The resulting output of the subset identification module 304 is shown in FIG. 3A as a set of layer subsets 306. For purposes of example, the set of layer subsets 306 is shown as containing three layer subsets 306a-c. Layer subset 306a may, for example, be the subsets 102a-e in layer 104a of FIG. 1; layer subset 306b may, for example, be the subsets 106a-d in layer 104b of FIG. 1; and layer subset 306c may, for example, be the subsets 108a-c in layer 104c of FIG. 1.

Referring to FIG. 3B, a dataflow diagram is shown of a system 350 for generating mappings of the kind illustrated in FIGS. 2A-2C according to one embodiment of the present invention. Referring to FIG. 4B, a flowchart is shown of a method 450 performed by the system 350 of FIG. 3B according to one embodiment of the present invention.

The system 350 (FIG. 3B) and method 450 (FIG. 4B) may operate as follows. The system 350 includes a string 352, such as the string 100 shown in FIG. 1. The system 350 also includes a layer generation module 354. In general, the layer generation module 354 generates a plurality of layers 356. By way of example, the layers 204a-c shown in FIGS. 2A-2C are examples of the layers 356 shown in FIG. 3B. More specifically, layers 356 includes layers 356a-c, in which layer 204a (FIG. 2A) is an example of layer 356a, layer 204b (FIG. 2B) is an example of layer 356b, and layer 204c (FIG. 2C) is an example of layer 356c.

The layer generation module 354 may generate the layers 356 in any of a variety of ways. For example, the method 450 of FIG. 4B may enter a loop over each of a plurality of layer indices i (FIG. 4B, operation 452). The values of i may be selected from any set, such as $\{1, 2\}$, $\{1, 2, 3\}$, $\{1, 2, 3, 4\}$, $\{2, 3\}$, or $\{2, 3, 4\}$.

For each value of i, the layer generation module 354 may identify (e.g., generate) a layer having layer index i, wherein each element in layer i contains exactly i symbols (FIG. 4B, operation 454). The layer generation module 354 may generate the elements within a particular layer in any of a variety of ways. For example, the layer generation module 354 may have access to a symbol alphabet 358. The symbol alphabet 358 may specify the set of symbols from which any string (e.g., string 352) may be generated. In the case of FIG. 1, in which the string 100 is a binary string, the symbol alphabet 358 may consist of two distinct symbols, e.g., $\{-1, +1\}$ or $\{0, 1\}$. In the case of strings representing DNA sequences, the symbol alphabet 358 may consist of four distinct symbols, e.g., $\{G, T, C, A\}$. In the case of strings representing protein sequences, the symbol alphabet 358 may consist of twenty distinct symbols, e.g., $\{R, K, D, E, Q, N, H, S, T, Y, C, M, W, A, I, L, F, V, P, G\}$. These particular symbol alphabets are merely examples and do not constitute limitations of the present invention.

The layer generation module 354 may use the symbol alphabet 358 to generate, within a particular layer having index i, a set of elements consisting of all possible combinations of i symbols selected from the symbol alphabet 358 (where a single symbol may be repeated within an element). For example, if i=2, the layer generation module 354 may generate, within layer 2, a set of two-symbol elements consisting of all possible combinations of two symbols selected from the symbol alphabet 358. If, for example, the symbol alphabet 358 defines the set $\{-1, +1\}$, then for i=2, the layer generation module may generate a layer containing the elements $-1-1$, $-1+1$, $+1-1$, and $+1+1$ (as represented by layer 204b in FIG. 2B).

The layer generation module 354 may repeat operation 454 for the remaining layers (FIG. 4B, operation 456). The resulting output of the layer generation module 354, as shown in FIG. 3B, is the set of layers 356.

Figure 3C:
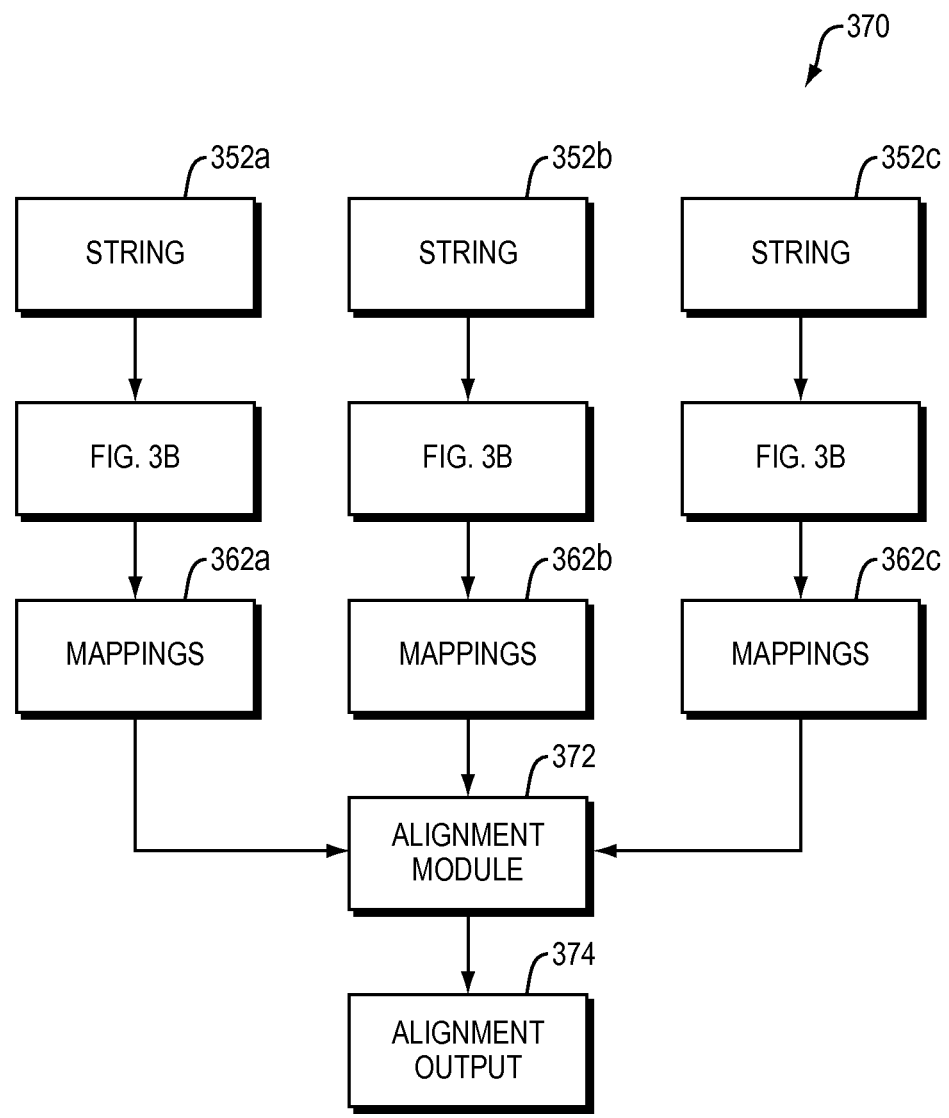
FIG. 3C is a diagram illustrating a system for aligning two or more strings with each other according to one embodiment of the present invention.
Figure 4A:
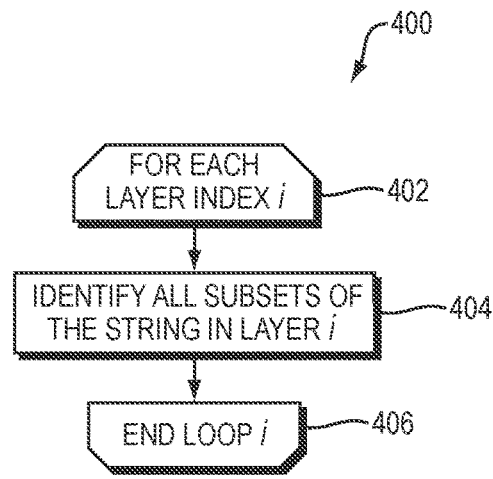
FIGS. 4A-4B are flowcharts of methods performed by the systems of FIGS. 3A-3B according to one embodiment of the present invention.
Figure 4B:
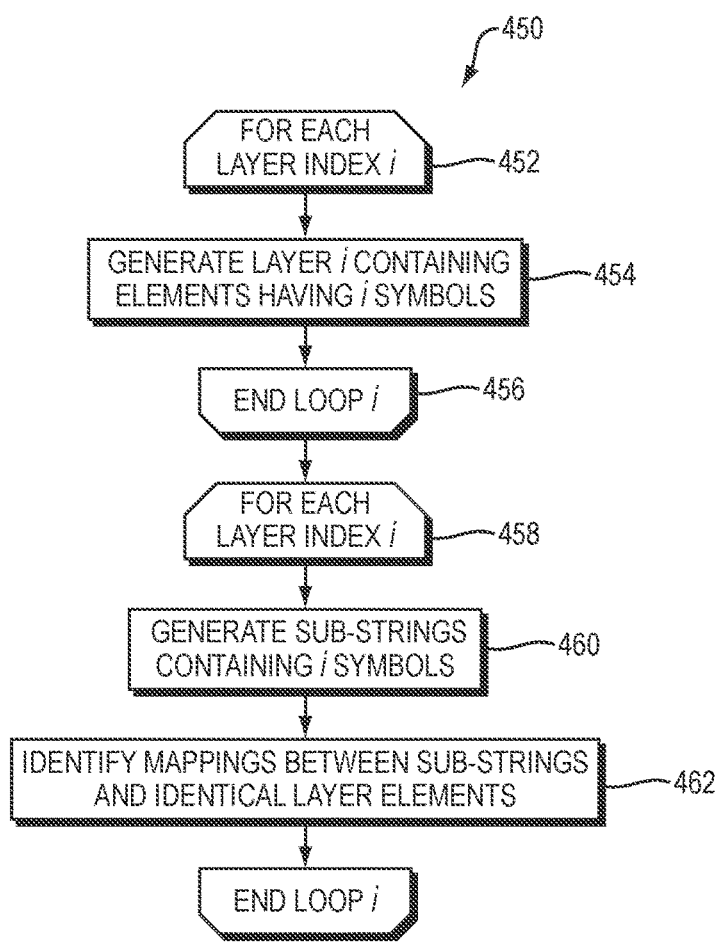

The system of FIG. 3B also includes a mapping identification module 360. In general, the mapping identification module 360 identifies mappings 362 between subsets of the string 352 and elements within the layers 356 generated by the layer generation module 354. The mapping identification module 360 may, for example, identify a set of such mappings for each layer in the layers 356. The mappings shown in FIGS. 2A-2C are examples of such mappings. For example, in the particular embodiment shown in FIG. 3B, the mapping identification module 360 has identified mappings 364a between subsets of string 352 and layer 356a; mappings 364b between subsets of string 352 and layer 356b; and mappings 364c between subsets of string 352 and layer 356c. The mappings 250a-e in FIG. 2A are examples of the mappings 364a in FIG. 3B; the mappings 254a-d in FIG. 2B are examples of the mappings 364b in FIG. 3B; and the mappings 258a-c in FIG. 2C are examples of the mappings 364c in FIG. 3C.

Referring again to FIG. 4B, the mapping identification module 360 may enter a loop over each of the layer indices i (or over any subset of such indices) (FIG. 4B, operation 458). The mapping identification module 360 may identify (e.g., generate) one or more sub-strings of the string 352, in which each of the sub-strings contains exactly i symbols (FIG. 4B, operation 460). Each such sub-string may, for example, consist of a consecutive set of symbols from the string 352. The mapping identification module 360 may, in operation 460, identify all sub-strings of the string 352 containing exactly i symbols or only a subset of such sub-strings.

For each of the sub-strings identified in operation 460, the mapping identification module 360 identifies (e.g., generates) a mapping between the sub-string and an element in layer i (within the layers 356) that is identical to the sub-string (FIG. 4B, operation 462). For example, if i=2 and the sub-string is 01, then the mapping identification module 360 may identify a mapping (e.g., mapping 254c in FIG. 2B) between the sub-string 01 (e.g., sub-string 106c in FIG. 2B) and the element 01 (e.g., element 256b in FIG. 2B) in layer 2. By repeating the operations described above, the mapping identification module 360 generates the mappings 362 based on the string 352 and the layers 356.

Once a string has been mapped to one or more layers using the techniques illustrated in FIGS. 3A-3B and 4A-4B, the resulting mappings may be used to align the string with one or more other strings.

Figure 4C:
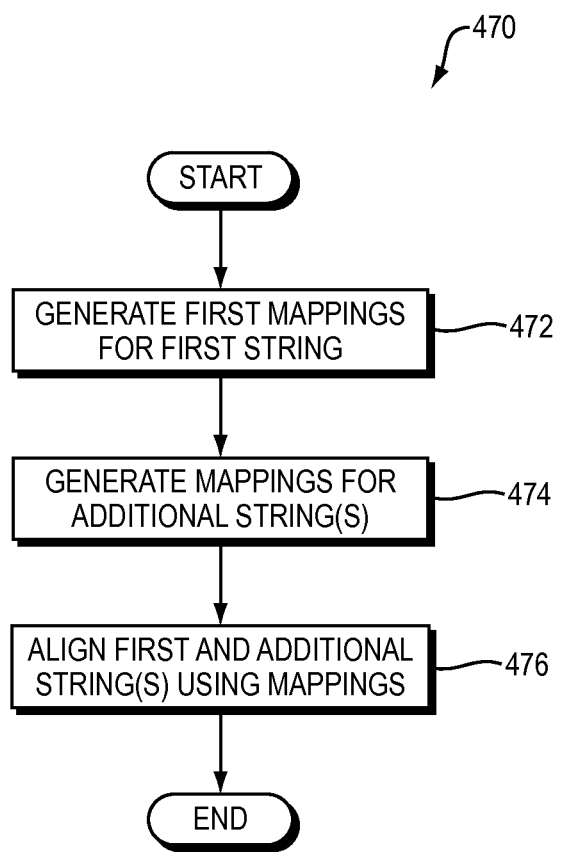
FIG. 4C is a flowchart of a method performed by the system of FIG. 3C according to one embodiment of the present invention.

In general, the system 370 of FIG. 3C contains two or more strings. In particular, a first string 352a, a second string 352b, and a third string 352c are shown in FIG. 3C for purposes of example. In general, however, the techniques of FIG. 3C may be applied to any number of strings (i.e., two, three, or more strings). Therefore, any references herein to aligning multiple strings should be understood to apply to aligning two or more strings. For example, the techniques that are shown in FIG. 3C in connection with three strings may be applied to two strings, three strings, or more than three strings. The system 370 of FIG. 3C aligns the first string 352a, the second string 352b, and the third string 352c with each other. More specifically, referring to the method 470 of FIG. 4C, the system 370 applies the techniques of FIGS. 3B and 4B to the first string 352a to produce mappings 362a of the first string 352a to one or more layers (FIG. 4C, operation 472). The system 370 applies the techniques of FIGS. 3B and 4B to the second string 352b to produce mappings 362b of the second string 352b to one or more layers (FIG. 4C, operation 474). The system 370 applies the techniques of FIGS. 3B and 4B to the third string 352c to produce mappings 362c of the third string 352c to one or more layers (FIG. 4C, operation 474). The system 370 includes an alignment module 372, which aligns the first string 352a, the second string 352b, and the third string 352c with each other using the first mappings 362a, the second mappings 362b, and the third mappings 362c, thereby producing alignment output 374 representing the results of aligning the first string 352a, the second string 352b, and the third string 352c with each other (FIG. 4C, operation 476). The system 370 and method 470 may align the strings 352a-c with each other in polynomial time, regardless of the number of strings aligned.

The alignment module 372 may align the strings 352a, 352b, and 352c in any of a variety of ways. The following description will refer to aligning only the first string 352a with the second string 352b for ease of explanation. However, the same techniques may be used to align any number of strings with each other. For example, recall that the system 370 has created mappings 362a for string 352a and mappings 362b for string 352b. Each of the mappings 362a and 362b may have the form and properties of the mappings 362 of FIG. 3B. For example, the mappings 362a associated with string 352a may include corresponding layer mappings having the form and properties of layer mappings 362a, 362b, and 362c, while the mappings 362b associated with string 352b may include corresponding layer mappings having the form and properties of layer mappings 362a, 362b, and 362c.

The layer mappings within the mappings 362a and 362b represents a hierarchical index of literals, words, and clauses in the strings 352a and 352b. For example, with respect to string 352a:
  the layer mappings 364a within the mappings 362a associated with string 352a indicate the positions within string 352a at which each −1 occurs, and the positions within string 352a at which each +1 occurs;
  the layer mappings 364b within the mappings 362a associated with string 352a indicate the positions within string 352a at which each word −1−1 occurs, the positions within string 352a at which each word −1+1 occurs, the positions within string 352a at which each word +1−1 occurs, and the positions within string 352a at which each word +1+1 occurs; and
  the layer mappings 364c within the mappings 362a associated with string 352a indicate the positions within string 352a at which each clause −1−1−1 occurs, the positions within string 352a at which each clause −1−1+1 occurs, the positions within string 352a at which each clause −1+1−1 occurs, the positions within string 352a at which each clause −1+1+1 occurs, the positions within string 352a at which each clause +1−1−1 occurs, the positions within string 352a at which each clause +1−1+1 occurs, the positions within string 352a at which each clause +1+1−1 occurs, and the positions within string 352a at which each clause +1+1+1 occurs.

Similarly, with respect to string 352b:
  the layer mappings 364a within the mappings 362b associated with string 352b indicate the positions within string 352b at which each −1 occurs, and the positions within string 352b at which each +1 occurs;
  the layer mappings 364b within the mappings 362b associated with string 352b indicate the positions within string 352b at which each word −1−1 occurs, the positions within string 352b at which each word −1+1 occurs, the positions within string 352b at which each word +1−1 occurs, and the positions within string 352b at which each word +1+1 occurs; and
  the layer mappings 364c within the mappings 362b associated with string 352b indicate the positions within string 352b at which each clause −1−1−1 occurs, the positions within string 352b at which each clause −1−1+1 occurs, the positions within string 352b at which each clause −1+1−1 occurs, the positions within string 352b at which each clause −1+1+1 occurs, the positions within string 352b at which each clause +1−1−1 occurs, the positions within string 352b at which each clause +1−1+1 occurs, the positions within string 352b at which each clause +1+1−1 occurs, and the positions within string 352b at which each clause +1+1+1 occurs.

The alignment module 372 may use such information about the locations of each literal, clause, and/or word in each of the strings 352a and 352b to align the two strings 352a and 352b. For example, consider a particular embodiment in which the alignment module 372 uses only the layer mappings 364c for the strings 352a and 352b. For example, the alignment module 372 may, for each 3-bit sequence C (i.e., clause) in the first string 352a, use the layer mappings 364c within the mappings 362b associated with the second string 352b to identify all occurrences (if any) of the clause C in the second string 352b. Such an operation may be performed in a fixed amount of time. For each match of clause C that the alignment module finds in the second string 352b, the alignment module may determine, based on the location of clause C in the first string 352a and the location of the matching clause in the second string 352b, whether the two instances of clause C are located at the same location in both strings 352a and 352b or at different locations. If they are at different locations, the alignment module 372 may identify a difference between the locations, such as by subtracting the location of clause C in string 352a from the location of clause C in string 352b.

The example just described involves finding exact matches for each clause of the first string 352a in the second string 352b. This is also referred to as finding the "intersection" of strings 352a and 352b. The alignment module 372 may perform other alignment operations, in addition to or instead of finding the intersection.

For example, the alignment module 372 may find, for each clause C in the first string 352a, all clauses in the second string 352b that are different than clause C. One way in which alignment module 372 may find such differences is by first finding the exact matches for clause C in the second string 352b, and then concluding that all clauses in the second string 352b that are not exact matches for clause C are different than clause C.

As another example, it may be of interest to identify contents in the second string 352b that are the complement of contents in the first string 352a. In the case of binary numbers, the complement of −1 is +1 and the complement of +1 is −1. In the case of other alphabets (such as an alphabet representing the amino acids), other complements may exist. The alignment module 372 may identify complements in any of a variety of ways. For example, the alignment module 372 may be configured, for each possible combination of clause $C_1$ and $C_2$, with knowledge of the complements of $C_1$ in $C_2$. For example, the alignment module 372 may be configured with knowledge that if $C_1$=−1+1−1 and $C_2$=−1−1+1, then there is no complement at the leftmost location (because −1 is not the complement of −1), that there is a complement at the middle location (because −1 is the complement of +1), and that there is a complement at the rightmost location (because +1 is the complement of −1).

The alignment module 372 may use any of the techniques disclosed above for all clauses C in the first string 352a to identify intersections (identical matches), differences, and/or complements of such clauses in the second string 352b, and to identify the locations of such intersections, differences, and/or complements in the second string 352b. The result is an alignment of the first string 352a with the second string 352b. Because the operations on each clause can be performed in a fixed amount of time, and because the number of operations required is equal to the number of clauses C, the alignment module 372 may perform the alignment in polynomial time.

As described above, the string 352a may be represented by a first three-dimensional representation of the kind shown in FIGS. 6A-6H, and the second string 352b may be represented by a first three-dimensional representation of the kind shown in FIGS. 6A-6H. For example, each bit in the string 352a may be mapped to one of the dimensions in the three-dimensional space 600 in a repeating pattern (e.g., x, y, z, x, y, z, etc.). Similarly, each bit in the string 352b may be mapped to one of the dimensions in the three-dimensional space 600 in the same repeating pattern.

For example, assume that the string 352a is the binary number +1+1+1−1−1−1. Such a binary number may be mapped to the x, y, and z dimensions in the following way: +1z+1y+1x−1z−1y−1x. Now assume that the string 352b is the binary number +1+1+1−1−1+1. Such a binary number may be mapped to the x, y, and z dimensions in the following way: +1x+1z+1y−1x−1z−1y+1x. As can be seen, the leftmost six bits of these two strings are identical to each other. The second string 352b, however, is shifted by one bit to the left with respect to the first string 352a, as indicated by the rightmost +1x bit of the second string 352b.

When performing the alignment method 470 of FIG. 4C on two such strings, the method 470 may determine both: (1) that the second string 352b contains an additional bit (namely, the rightmost bit +1x) which the first string 352a does not contain; and (2) that the leftmost six bits of the second string 352b are identical to the bits of the first string 352a, except that the leftmost six bits of the second string 352b are shifted by one bit to the left relative to the bits of the first string 352a. The method 470 may make this second determination by reference to the spatial coordinates of the first and second strings 352a-b, i.e., by reference to the x, y, and z dimensions to which the bits of the first and second strings 352a-b have been mapped. For example, it can be seen that although both the first and second strings 352a-b contain the six bits +1+1+1−1−1−1, these bits are mapped to the dimensions zyxzyx in the first string 352a and to the dimensions xzyxzy in the second string 352b. The alignment method 470 of FIG. 4C may compare these dimension mappings to each other do determine that the bits of the first string 352a have been shifted by one position to the left in the second string 352b.

It is important to both compare the values of the bits in the strings 352a-b and the spatial positions of those bits because it is not only differences in values but also differences in spatial positions that can be significant. For example, if the strings 352a-b represent proteins, the presence of the same bit sequence (e.g., +1+1+1−1−1−1) at different spatial positions in the two strings 352a-b can indicate the presence of a genetic disorder or other defect. Such a problem cannot be detected merely by comparing the values of the bits in the two strings 352a-b. Instead, detecting such a problem requires also comparing the spatial positions of the bits in the two strings 352a-b. Embodiments of the present invention which represent the strings 352a-b as three-dimensional structures (such as of the kinds shown in FIGS. 6A-6H) can assist in making such comparisons.

Embodiments of the present invention may produce output 374 representing the results of an alignment in any of a variety of ways. For example, embodiments of the present invention may represent the results of the alignment using text strings representing the similarities and differences between the first string 352a and the second string 352b, or by using colors to represent the differences between the first string 352*a* and the second string 352*b*. More generally, embodiments of the present invention may produce output 374 having any of the forms commonly used to represent intersections, differences, and/or complements in sequence alignments.

Embodiments of the present invention have a variety of advantages. For example, one advantage of embodiments of the present invention is that they may be used to align sequences extremely rapidly. Consider, for example, the problem of aligning a sequence containing 500 binary elements. To search a knowledgebase exhaustively for all possible sequences of this length would require $2^{500}$ operations. Such a search clearly is computationally infeasible.

In contrast, embodiments of the present invention may be used to decompose the sequence into layers in the manner described above. Assume, for example, that the sequence is decomposed into clauses, each of which consists of three binary elements. Because each such clause has only eight ($2^3$) possible values, a search may be performed for each such clause using only a maximum of eight operations. Therefore, if the number of clauses to be searched is n, then a search for the entire sequence may be performed in 8n operations. In the example above, in which the sequence contains 500 elements, the number of operations required would be approximately 1,333. As can be seen from this example, embodiments of the present invention may be used to search for sequences in a knowledgebase, and thereby perform sequence alignment, much more rapidly than is possible when performing an exhaustive search.

Another advantage of embodiments of the present invention is that they may be used to perform alignment precisely on an element-by-element basis. In other words, embodiments of the present invention may be used to determine whether each and every element in a first sequence is the same as or different from each and every element in a second sequence, and to produce output representing those similarities and differences for each element in the first sequence. This is a significant benefit in comparison to alignment techniques that perform alignment only on a statistical basis, and which therefore only produce output indicating the statistical degree of similarity between two sequences (e.g., 5% or 90%). Embodiments of the present invention may be used to provide such precise alignment at the very high speeds described above.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

The invention claimed is:

1. A method performed by at least one computer processor executing computer program instructions stored on at least one computer-readable medium, the method comprising:
 (1) receiving a first sentence, the first sentence comprising a first ordered sequence of symbols representing at least one of a protein sequence, a DNA sequence, and an RNA sequence;
 (2) storing the first sentence in a first computer-readable memory and a second computer-readable memory using values of +1 and −1, comprising:
  (2)(a) storing data, having values of +1 and −1, representing a first plurality of perceptions in the first computer-readable memory, wherein the first plurality of perceptions comprises a first plurality of instances of a first plurality of classes;

(2)(b) storing data, having values of +1 and −1, representing a first plurality of conceptions in the second computer-readable memory, wherein the first plurality of conceptions comprises the first plurality of classes; and (2)(c) storing, in at least one of the first computer-readable memory and the second computer-readable memory, data representing a first plurality of relationships between the first plurality of perceptions and the first plurality of conceptions, wherein the first plurality of relationships includes membership of the first plurality of instances within the first plurality of classes;

(3) identifying a first plurality of overlapping clauses in the first sentence, wherein each of the first plurality of clauses consists of three consecutive elements, each having a value of +1 or −1, in the first sentence;

(4) creating and storing, in at least one of the first computer-readable memory and the second computer-readable memory, a first index of locations of occurrence of each clause in the first plurality of clauses in the first sentence;

(5) receiving a second sentence, the second sentence comprising a second ordered sequence of symbols;

(6) storing the second sentence in the first computer-readable memory using values of +1 and −1, comprising:

(6)(a) storing data, having values of +1 and −1, representing a second plurality of perceptions in the first computer-readable memory, wherein the second plurality of perceptions comprises a second plurality of instances of a second plurality of classes;

(6)(b) storing data, having values of +1 and −1, representing a second plurality of conceptions in the second computer-readable memory, wherein the second plurality of conceptions comprises the second plurality of classes; and (6)(c) storing, in at least one of the first computer-readable memory and the second computer-readable memory, data representing a second plurality of relationships between the second plurality of perceptions and the second plurality of conceptions, wherein the second plurality of relationships includes membership of the second plurality of instances within the second plurality of classes;

(7) identifying a second plurality of overlapping clauses in the second sentence, wherein each of the second plurality of clauses consists of three elements, each having a value of +1 or −1, in the first sentence;

(8) creating and storing, in at least one of the first computer-readable memory and the second computer-readable memory, a second index of locations of occurrence of each clause in the second plurality of clauses in the second sentence;

(9) aligning the first sentence with the second sentence based on the first index and the second index, comprising comparing the first plurality of relationships to the second plurality of relationships; and

(10) producing alignment output representing a result of aligning the first sentence with the second sentence, wherein the alignment output contains data representing at least one similarity between the first sentence and the second sentence and data representing at least one difference between the first sentence and the second sentence.

2. The method of claim 1, wherein (9) comprises finding clauses in the second sentence that are identical to clauses in the first sentence.

3. The method of claim 1, wherein (9) comprises finding clauses in the second sentence that are different than clauses in the first sentence.

4. The method of claim 1, wherein (9) comprises finding elements in the second sentence that are complements of elements in the first sentence.

5. The method of claim 1, wherein (9) comprises:
(9)(a) creating a three dimensional representation of the first sentence and a three dimensional representation of the second sentence; and
(9)(b) aligning the first sentence with the second sentence based on the three dimensional representation of the first sentence and the three dimensional representation of the second sentence.

6. A system comprising at least one non-transitory computer-readable medium having computer program instructions stored thereon, wherein the computer program instructions are executable by at least one computer processor to perform a method, the method comprising:

(1) receiving a first sentence, the first sentence comprising a first ordered sequence of symbols representing at least one of a protein sequence, a DNA sequence, and an RNA sequence;

(2) storing the first sentence in a first computer-readable memory and a second computer-readable memory using values of +1 and −1, comprising:

(2)(a) storing data, having values of +1 and −1, representing a first plurality of perceptions in the first computer-readable memory, wherein the first plurality of perceptions comprises a first plurality of instances of a first plurality of classes;

(2)(b) storing data, having values of +1 and −1, representing a first plurality of conceptions in the second computer-readable memory, wherein the first plurality of conceptions comprises the first plurality of classes; and (2)(c) storing, in at least one of the first computer-readable memory and the second computer-readable memory, data representing a first plurality of relationships between the first plurality of perceptions and the first plurality of conceptions, wherein the first plurality of relationships includes membership of the first plurality of instances within the first plurality of classes;

(3) identifying a first plurality of overlapping clauses in the first sentence, wherein each of the first plurality of clauses consists of three consecutive elements, each having a value of +1 or −1, in the first sentence;

(4) creating and storing, in at least one of the first computer-readable memory and the second computer-readable memory, a first index of locations of occurrence of each clause in the first plurality of clauses in the first sentence;

(5) receiving a second sentence, the second sentence comprising a second ordered sequence of symbols;

(6) storing the second sentence in the first computer-readable memory using values of +1 and −1, comprising:

(6)(a) storing data, having values of +1 and −1, representing a second plurality of perceptions in the first computer-readable memory, wherein the second plurality of perceptions comprises a second plurality of instances of a second plurality of classes;

(6)(b) storing data, having values of +1 and −1, representing a second plurality of conceptions in the second computer-readable memory, wherein the second plurality of conceptions comprises the second plurality of classes; and (6)(c) storing, in at least one of the first computer-readable memory and the second computer-readable memory, data representing a second plurality of relationships between the second plurality of perceptions and the second plurality of conceptions, wherein the second plurality of relationships includes membership of the second plurality of instances within the second plurality of classes;

(7) identifying a second plurality of overlapping clauses in the second sentence, wherein each of the second plurality of clauses consists of three elements, each having a value of +1 or −1, in the first sentence;

(8) creating and storing, in at least one of the first computer-readable memory and the second computer-readable memory, a second index of locations of occurrence of each clause in the second plurality of clauses in the second sentence;

(9) aligning the first sentence with the second sentence based on the first index and the second index, comprising comparing the first plurality of relationships to the second plurality of relationships; and

(10) producing alignment output representing a result of aligning the first sentence with the second sentence, wherein the alignment output contains data representing at least one similarity between the first sentence and the second sentence and data representing at least one difference between the first sentence and the second sentence.

7. The system of claim 6, wherein (9) comprises finding clauses in the second sentence that are identical to clauses in the first sentence.

8. The system of claim 6, wherein (9) comprises finding clauses in the second sentence that are different than clauses in the first sentence.

9. The system of claim 6, wherein (9) comprises finding elements in the second sentence that are complements of elements in the first sentence.

10. The system of claim 6, wherein (9) comprises:

(9)(a) creating a three dimensional representation of the first sentence and a three dimensional representation of the second sentence; and (9)(b) aligning the first sentence with the second sentence based on the three dimensional representation of the first sentence and the three dimensional representation of the second sentence.

* * * * *